(12) United States Patent
Igarashi et al.

(10) Patent No.: US 6,808,827 B2
(45) Date of Patent: Oct. 26, 2004

(54) LIGHT-EMITTING DEVICE AND IRIDIUM COMPLEX

(75) Inventors: Tatsuya Igarashi, Kanagawa (JP); Keizo Kimura, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 104 days.

(21) Appl. No.: 09/956,007

(22) Filed: Sep. 20, 2001

(65) Prior Publication Data

US 2002/0048689 A1 Apr. 25, 2002

(30) Foreign Application Priority Data

Sep. 21, 2000 (JP) .................................... P. 2000-287178
Jul. 19, 2001 (JP) .................................... P. 2001-219909

(51) Int. Cl.⁷ .......................... H05B 33/14; C09K 11/06
(52) U.S. Cl. ...................... 428/690; 428/917; 313/504; 313/506; 257/102; 257/103; 252/301.16; 546/4; 556/13
(58) Field of Search ................... 428/690, 917; 313/504, 506; 257/102, 103; 252/301.16; 546/2, 4; 556/13, 18, 19, 20, 21, 22, 23

(56) References Cited

U.S. PATENT DOCUMENTS

| | | | | |
|---|---|---|---|---|
| 5,707,745 A | * | 1/1998 | Forrest et al. | ............... 428/432 |
| 2002/0121638 A1 | * | 9/2002 | Grushin et al. | ................ 257/40 |
| 2002/0182441 A1 | * | 12/2002 | Lamansky et al. | ........... 428/690 |
| 2002/0190250 A1 | * | 12/2002 | Grushin et al. | ................ 257/40 |

FOREIGN PATENT DOCUMENTS

| | | | |
|---|---|---|---|
| WO | 00/41512 | 7/2000 | |
| WO | 00/57676 | 9/2000 | ........... H05B/33/12 |
| WO | 00/70655 | 11/2000 | |

OTHER PUBLICATIONS

Tang, C.W., "Organic electroluminescent diodes" Appl. Phys. Lett. 51 (12), Sep. 21, 1987, pp. 913–915.

Baldo, M.A., "Very high-efficiency green organic light-emitting devices based on electrophosphorescence", Applied Physics Letters, vol. 75, No. 1, Jul. 5, 1999, pp. 4–6.

* cited by examiner

Primary Examiner—Marie Yamnitzky
(74) Attorney, Agent, or Firm—Sughrue Mion, PLLC

(57) ABSTRACT

A light-emitting device comprising a pair of electrodes, and organic compound layers comprising a light-emitting layer provided in between the electrodes, wherein at least one of the organic compound layers comprises a compound having a transition metal atom-phosphorus atom bond.

50 Claims, No Drawings

LIGHT-EMITTING DEVICE AND IRIDIUM COMPLEX

FIELD OF THE INVENTION

This invention relates to a material for a light-emitting device which can convert electric energy to light, and to a light-emitting device which can suitably be utilized in the field of display device, display, back light, electrophotography, light source for illumination, light source for recording, light source for exposure, light source for readout, mark, billboard, interior decoration, optical communication and the like. In addition, it relates to an iridium complex showing a strong emission in a blue region.

BACKGROUND OF THE INVENTION

At the present time, development and study on various display devices are aggresively driven. In particular, organic electric field light-emitting (EL) can obtain highly bright luminescence at a low voltage and accordingly, is drawing attention as a promising display device. For example, a light-emitting device comprising an organic thin film formed by depositing an organic compound is known (Applied Physics Letters, Vol. 51, page 913 (1987). The light-emitting device described in this publication has a laminate structure wherein a tris(8-hydroxyquinolinato)aluminum complex (Alq) is used as an electron transporting material and is layered on a hole transporting material (an amine compound), and is greatly improved in the luminescence properties due to the structure as compared with conventional single-layer devices.

In recent years, it has actively been investigated to apply organic EL devices to color display or white light source. However, in order to develop high performance color display and white light source, it is necessary to improve properties of each of blue light-emitting devices, green light-emitting devices and red light-emitting devices.

As a means for improving the properties of light-emitting devices, a green light-emitting device utilizing luminescence emitted from an ortho-metalated iridium complex (Ir(ppy)$_3$: Tris-Ortho-Metalated Complex of Iridium(III) with 2-Phenylpyridine) has been reported (Applied Physics Letters 75, 4 (1999)). However, since Ir(ppy)$_3$ emits only green light, it can be applied to only a limited scope of display. Thus, development of devices capable of emitting other color light (blue or red light) with a high efficiency have been required.

SUMMARY OF THE INVENTION

The present invention provides a light-emitting device with a high efficiency, and provides a novel metal complex capable of actualizing the device.

The above-described subjects of the invention can be solved by the following:
(1) A light-emitting device comprising:
  a pair of electrodes; and
  organic compound layers comprising a light-emitting layer provided in between the electrodes,
  wherein at least one of the organic compound layers comprises a compound having a transition metal atom-phosphorus atom bond.
(2) The light-emitting device set forth in (1) above, wherein the compound having a transition metal atom-phosphorus atom bond is represented by the following formula (2):

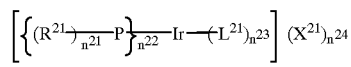

(2)

wherein $R^{21}$ represents a hydrogen atom or a substituent, $L^{21}$ represents a ligand, $X^{21}$ represents a counter ion, $n^{21}$ represents 2 or 3, $n^{22}$ represents an integer of 1 to 8, $n^{23}$ represents an integer of 0 to 8, $n^{24}$ represents an integer of 0 to 6, and, when $n^{21}$, $n^{22}$, $n^{23}$ or $n^{24}$ represents a plural number, $R^{21}$ groups, $(R^{21})_{n21}$—P ligands, $L^{21}$ ligands or $X^{21}$ ions are each the same or different.
(3) The light-emitting device set forth in (1) above, wherein the compound having a transition metal atom-phosphorus atom bond is a compound having a maximum emitted wavelength, λmax, in a range of 350 nm to 550 nm.
(4) The light-emitting device set forth in (1) above, wherein the layer comprising the compound having a transition metal atom-phosphorus atom bond is a layer formed by a coating process.
(5) The light-emitting device set forth in (1) above, wherein the compound having a transition metal atom-phosphorus atom bond is represented by the following formula (4):

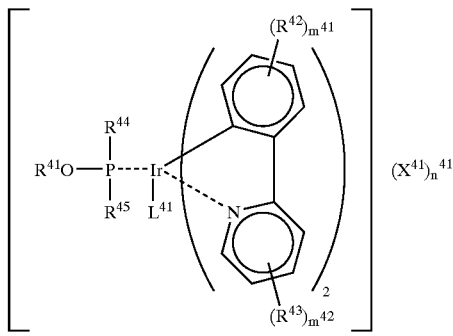

(4)

wherein $R^{41}$, $R^{42}$, $R^{43}$, $R^{44}$ and $R^{45}$ each independently represent a substituent, $L^{41}$ represents a ligand, $X^{41}$ represents a counter anion, $m^{41}$ and $m^{42}$ each independently represent an integer of 0 to 4, and $n^{41}$ represents 0 or 1.
(6) The light-emitting device set forth in (1) above, wherein the compound having a transition metal atom-phosphorus atom bond is represented by the following formula (5):

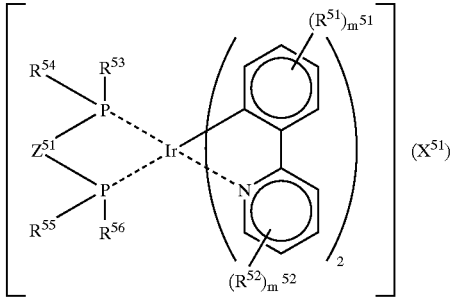

(5)

wherein $R^{51}$, $R^{52}$, $R^{53}$, $R^{54}$, $R^{55}$ and $R^{56}$ each independently represent a substituent, $Z^{51}$ represents a linkage group, $X^{51}$ represents a counter anion, and $m^{51}$ and $m^{52}$ each independently represent an integer of 0 to 4.

(7) The light-emitting device set forth in (1) above, wherein the compound having a transition metal atom-phosphorus atom bond is represented by the following formula (6):

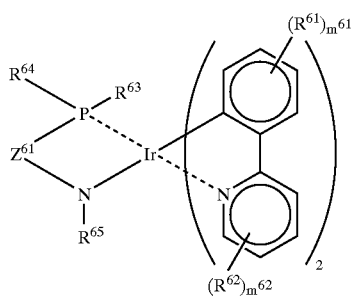

(6)

wherein $R^{61}$, $R^{62}$, $R^{63}$, $R^{64}$ and $R^{65}$ each independently represent a substituent, $Z^{61}$ represents a linkage group, and $m^{61}$ and $m^{62}$ each independently represent an integer of 0 to 4.

(8) The light-emitting device set forth in (5) above, wherein $L^{41}$ represents a halogen atom or a cyano group.

(9) The light-emitting device set forth in (6) above, wherein $Z^{51}$ represents an alkylene group or an arylene group.

(10) The light-emitting device set forth in (7) above, wherein $Z^{61}$ represents an alkylene group or an arylene group.

(11) The light-emitting device set forth in (5) above, wherein the compound represented by the formula (4) has a maximum emitted wavelength, λmax, in a range of 350 nm to 550 nm.

(12) The light-emitting device set forth in (6) above, wherein the compound represented by the formula (5) has a maximum emitted wavelength, λmax, in a range of 350 nm to 550 nm.

(13) The light-emitting device set forth in (7) above, wherein the compound represented by the formula (6) has a maximum emitted wavelength, λmax, in a range of 350 nm to 550 nm.

(14) The light-emitting device set forth in (5) above, wherein the layer comprising the compound represented by the formula (4) is a layer formed by a coating process.

(15) The light-emitting device set forth in (6) above, wherein the layer comprising the compound represented by the formula (5) is a layer formed by a coating process.

(16) The light-emitting device set forth in (7) above, wherein the layer comprising the compound represented by the formula (6) is a layer formed by a coating process.

(17) A compound represented by the following formula (4):

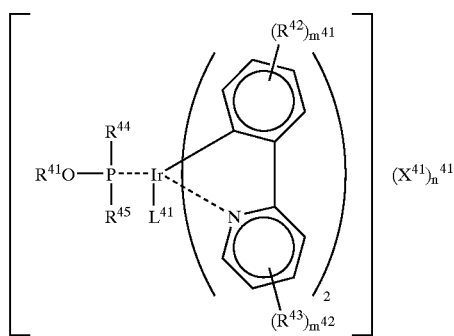

(4)

wherein $R^{41}$, $R^{42}$, $R^{43}$, $R^{44}$ and $R^{45}$ each independently represent a substituent, $L^{41}$ represents a ligand, $X^{41}$ represents a counter anion, $m^{41}$ and $m^{42}$ each independently represent an integer of 0 to 4, and $n^{41}$ represents 0 or 1.

(18) A compound represented by the following formula (5):

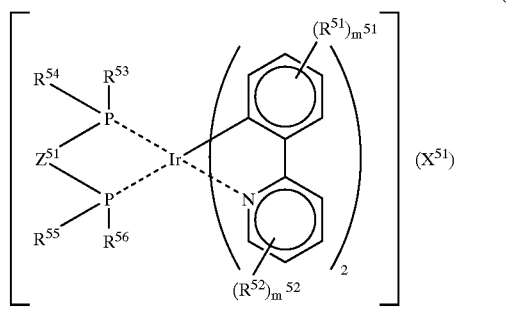

(5)

wherein $R^{51}$, $R^{52}$, $R^{53}$, $R^{54}$, $R^{55}$ and $R^{56}$ each independently represent a substituent, $Z^{51}$ represents a linkage group, $X^{51}$ represents a counter anion, and $m^{51}$ and $m^{52}$ each independently represent an integer of 0 to 4.

(19) A compound represented by the following formula (6):

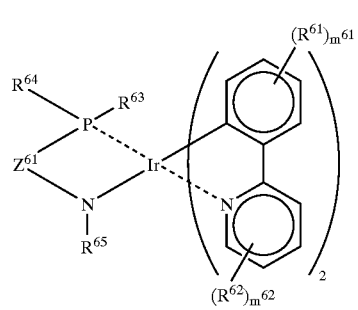

(6)

wherein $R^{61}$, $R^{62}$, $R^{63}$, $R^{64}$ and $R^{65}$ each independently represent a substituent, $Z^{61}$ represents a linkage group, and $m^{61}$ and $m^{62}$ each independently represent an integer of 0 to 4.

(20) The light-emitting device set forth in (1) above, wherein the transition metal atom is an atom selected from the group consisting ruthenium, rhodium, palladium, tungsten, rhenium, osmium, iridium and platinum.

(21) The light-emitting device set forth in (1) above, wherein the phosphorus atom constitutes a part of phosphorus ligand.

(22) The light-emitting device set forth in (21) above, wherein the phosphorus ligand is selected from the group consisting of an alkylphosphine and derivatives thereof, an arylphosphine and derivatives thereof, heteroarylphosphine and derivatives thereof, an alkoxyphosphine and derivatives thereof, an aryloxyphosphine and derivatives thereof, a heteroaryloxyaminophosphine and derivatives thereof, a phosphinine (phosphabenzene) and derivatives thereof, and aminophosphine and derivatives thereof.

(23) The light-emitting device set forth in (1) above, wherein x value on the CIE chromaticity diagram of the emitting is 0.22 or less, and y value on the CIE chromaticity diagram of the emitting is 0.53 or less.

(24) The light-emitting device set forth in (1) above, which emits spectrum having a half band width of 1 nm to 100 nm.

(25) The light-emitting device set forth in (2) above, wherein the valence number of iridium is trivalent.

(26) The light-emitting device set forth in (1) above, wherein the content of the compound having a transition metal atom-phosphorus atom bond in the light-emitting layer is from 0.1% to 100% by weight based on the total composition of the light-emitting layer.

(27) The light-emitting device set forth in (1) above, wherein the content of the compound having a transition metal atom-phosphorus atom bond in the light-emitting layer is from 1% to 50% by weight based on the total composition of the light-emitting layer.

(28) The light-emitting device set forth in (1) above, wherein the content of the compound having a transition metal atom-phosphorus atom bond in the light-emitting layer is from 5% to 30% by weight based on the total composition of the light-emitting layer.

DETAILED DESCRIPTION OF THE INVENTION

The invention is described below in detail.

A light-emitting device according to the invention contains a compound having at least one bond formed between transition metal atom and phosphorus atom (hereinafter abbreviated as "present compound"). The present compound is not particularly limited in its transition metal atom, but it is preferable that the transition metal atom be ruthenium, rhodium, palladium, tungsten, rhenium, osmium, iridium or platinum, more preferably rhenium, iridium or platinum.

The phosphorus atom binding to one of these transition metal atom preferably constitutes a part of phosphorus ligand.

As to the phosphorus ligand, the invention has no particular limitation, but a wide variety of known phosphorus ligands and derivatives thereof can be used (with examples including the ligands described, e.g., in G. Wilkinson, *Comprehensive Coordination Chemistry*, Pergamon Press Co. (1987), H. Yersin, *Photochemistry and Photophysics of Coordination Compounds*, Springer-Verlag A. G. (1987), and Akio Yamamoto, *Yuki Kinzoku Kagagu—Kiso to Oyo—* (which may be translated "Organometallic Chemistry—Fundamentals and Applications—"), Shokabo Co. (1982). Suitable examples of a phosphorus ligand contained in the present compound include an alkylphosphine and derivatives thereof, an arylphosphine and derivatives thereof, heteroarylphosphine and derivatives thereof, an alkoxyphosphine and derivatives thereof, an aryloxyphosphine and derivatives thereof, a heteroaryloxyaminophosphine and derivatives thereof, a phosphinine (phosphabenzene) and derivatives thereof, and aminophosphine and derivatives thereof.

Besides a phosphorus ligand as recited above, the present compound can have various known ligands (e.g., the ligands as described in G. Wilkinson, *Comprehensive Coordination Chemistry*, Pergamon Press Co. (1987), H. Yersin, *Photochemistry and Photophysics of Coordination Compounds*, Springer-Verlag A. G. (1987), and Akio Yamamoto, *Yuki Kinzoku Kagaku*—Kiso to Oyo— (which means "Organometallic Chemistry—Fundamentals and Applications—"), Shokabo Co. (1982)). Suitable examples of such ligands include halogen ligands (preferably chlorine ligand), nitrogen-containing heterocycle ligands (e.g., phenylpyridine, benzoquinoline, quinolinole, bipyridyl, phenanthroline), diketone ligands (e.g., acetylacetone), carboxylate ligands (e.g., acetic acid ligand), a carbon monoxide ligand, an isonitrile ligand and a cyano ligand. Of these ligands, nitrogen-containing heterocycle ligands are preferred over the others.

The present compound may contain one transition metal atom, or it may be the so-called polynuclear complex wherein two or more transition metal atoms are present. Further, the present compound may contain other metal atoms in addition to transition metal atom.

It is appropriate that the present compound have a maximum emitted wavelength ranging from 350 nm to 550 nm, preferably from 380 nm to 500 nm, particularly preferably from 400 nm to 480 nm.

From the viewpoint of blue color purity of luminescence color, it is more advantageous that the smaller x and y values the light-emitting device containing the present compound has on the CIE chromaticity diagram. More specifically, the suitable x value on the CIE chromaticity diagram of the luminescence is at most 0.22, preferably at most 0.20; while the suitable y value on the CIE chromaticity diagram of the luminescence is at most 0.53, preferably at most 0.50, particularly preferably at most 0.40.

From the viewpoint of blue color purity, it is also favorable that the luminescence spectrum of the light-emitting device containing the present compound has a half width of 1 to 100 nm, preferably 5 to 90 nm, more preferably 10 to 80 nm, particularly preferably 20 to 70 nm.

The present compound is preferably embodied in compounds represented by formula (1).

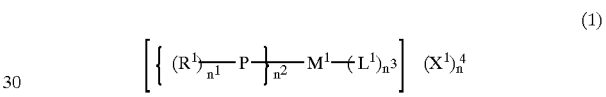

(1)

The compounds represented by formula (1) are illustrated below.

$R^1$ represents a hydrogen atom or a substituent, $M^1$ represents a transition metal ion, $L^1$ represents a ligand, and $X^1$ represents a counter ion. $n^1$ represents 2 or 3, $n^2$ represents an integer of 1 to 8, $n^3$ represents an integer of 0 to 8, and $n^4$ represents an integer of 0 to 6. When at least one of $n^1$, $n^2$, $n^3$ and $n^4$ is more than one, corresponding two or more $R^1$ groups, two or more $(R^1)_{n1}$—P ligands, two or more $L^1$ ligands and two or more $X^1$ ions may be each individually the same or different. $(R^1)_{n1}$—P ligands, $L^1$ ligands, or $(R^1)_{n1}$—P and $L^1$ ligands may combine with each other and form a chelate ligand.

Suitable examples of a substituent represented by $R^1$ include an alkyl group containing preferably 1 to 30 carbon atoms, more preferably 1 to 20 carbon atoms, particularly preferably 1 to 10 carbon atoms (e.g., methyl, ethyl, isopropyl, tert-butyl, n-octyl, n-decyl, n-hexadecyl, cyclopropyl, cyclopentyl, cyclohexyl), an alkenyl group containing preferably 2 to 30 carbon atoms, more preferably 2 to 20 carbon atoms, particularly preferably 2 to 10 carbon atoms (e.g., vinyl, allyl, 2-butenyl, 3-pentenyl), an alkynyl group containing preferably 2 to 30 carbon atoms, more preferably from 2 to 20 carbon atoms, particularly preferably 2 to 10 carbon atoms (e.g., propargyl, 3-pentynyl), an aryl group containing preferably 6 to 30 carbon atoms, more preferably 6 to 20 carbon atoms, particularly 6 to 12 carbon atoms (e.g., phenyl, p-methylphenyl, naphthyl, anthranyl), an amino group containing preferably 0 to 30 carbon atoms, more preferably 0 to 20 carbon atoms, particularly preferably 0 to 10 carbon atoms (e.g., amino, methylamino, dimethylamino, diethylamino, dibenzylamino, diphenylamine, ditolylamino), an alkoxy group containing preferably 1 to 30 carbon atoms, more preferably 1 to 20 carbon atoms, particularly preferably 1 to 10 carbon atoms (e.g., methoxy, ethoxy, butoxy, 2-ethylhexyloxy), an aryloxy group containing preferably 6 to 30 carbon atoms, more preferably 6 to 20 carbon atoms, particularly preferably 6 to 12 carbon atoms (e.g., phenyloxy, 1-naphthyloxy, 2-naphthyloxy), a heteroaryloxy group containing preferably 1 to 30 carbon atoms, more preferably 1 to 20 carbon atoms, particularly preferably 1 to 12 carbon atoms (e.g., pyridyloxy, pyrazyloxy, pyrimidyloxy, quinolyloxy), an acyl group containing preferably 1 to 30 carbon atoms, more preferably 1 to 20 carbon atoms, particularly preferably 1 to 12 carbon atoms (e.g., acetyl, benzoyl, formyl, pivaroyl), an alkoxycarbonyl group containing preferably 2 to 30 carbon atoms, more preferably 2 to 20 carbon atoms, particularly preferably 2 to 12 carbon atoms (e.g., methoxycarbonyl, ethoxycarbonyl), an aryloxycarbonyl group containing preferably 7 to 30 carbon atoms, more preferably 7 to 20 carbon atoms, particularly preferably 7 to 12 carbon atoms (e.g., phenyloxycarbonyl), an acyloxy group containing preferably 2 to 30 carbon atoms, more preferably 2 to 20 carbon atoms, particularly preferably 2 to 10 carbon atoms (e.g., acetoxy, benzoyloxy), an acylamino group containing preferably 2 to 30 carbon atoms, more preferably 2 to 20 carbon atoms, particularly preferably 2 to 10 carbon atoms (e.g., acetylamino, benzoylamino), an alkoxycarbonylamino group containing preferably 2 to 30 carbon atoms, more preferably 2 to 20 carbon atoms, particularly preferably 2 to 12 carbon atoms (e.g., methoxycarbonylamino), an aryloxycarbonylamino group containing preferably 7 to 30 carbon atoms, more preferably 7 to 20 carbon atoms, particularly preferably 7 to 12 carbon atoms (e.g., phenyloxycarbonylamino), a sulfonylamino group containing preferably 1 to 30 carbon atoms, more preferably 1 to 20 carbon atoms, particularly preferably 1 to 12 carbon atoms (e.g., methanesulfonylamino, benzenesulfonylamino), a sulfamoyl group containing preferably 0 to 30 carbon atoms, more preferably 0 to 20 carbon atoms, particularly preferably 0 to 12 carbon atoms (e.g., sulfamoyl, methylsulfamoyl, dimethylsulfamoyl, phenylsulfamoyl), a carbamoyl group containing preferably 1 to 30 carbon atoms, more preferably 1 to 20 carbon atoms, particularly preferably 1 to 12 carbon atoms (e.g., carbamoyl, methylcarbamoyl, diethylcarbamoyl, phenylcarbamoyl), an alkylthio group containing preferably 1 to 30 carbon atoms, more preferably 1 to 20 carbon atoms, particularly preferably 1 to 12 carbon atoms (e.g., methylthio, ethylthio), an arylthio group containing preferably 6 to 30 carbon atoms, more preferably 6 to 20 carbon atoms, particularly preferably 6 to 12 carbon atoms (e.g., phenylthio), a heteroarylthio group containing preferably 1 to 30 carbon atoms, more preferably 1 to 20 carbon atoms, particularly preferably 1 to 12 carbon atoms (e.g., pyridylthio, 2-benzimidazolylthio, 2-benzoxazolylthio, 2-benzothiazolylthio), a sulfonyl group containing preferably 1 to 30 carbon atoms, more preferably 1 to 20 carbon atoms, particularly preferably 1 to 12 carbon atoms (e.g., mesyl, tosyl), a sulfinyl group containing preferably 1 to 30 carbon atoms, more preferably 1 to 20 carbon atoms, particularly preferably 1 to 12 carbon atoms (e.g., methanesulfinyl or benzenesulfinyl), an ureido group containing preferably 1 to 30 carbon atoms, more preferably 1 to 20 carbon atoms, particularly preferably 1 to 12 carbon atoms (e.g., ureido, methylureido, phenylureido), a phosphoric acid amido group containing preferably 1 to 30 carbon atoms, more preferably 1 to 20 carbon atoms, particularly preferably 1 to 12 carbon atoms (e.g., diethylphosphoric acid amido, phenylphosphoric acid amido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, a heterocyclic group (including aliphatic heterocyclic groups and heteroaryl groups, and containing preferably 1 to 30, more preferably 1 to 12 carbon atoms, and hetero atom or atoms such as nitrogen atom, oxygen atom or sulfur atom, specific examples including imidazolyl, pyridyl, quinolyl, furyl, thienyl, piperidyl, morpholino, benzoxazolyl, benzimidazolyl, benzothiazolyl and carbamoyl), a silyl group containing preferably 3 to 40 carbon atoms, more preferably 3 to 30 carbon atoms, particularly preferably 3 to 24 carbon atoms (e.g., trimethylsilyl, triphenylsilyl), and a phosphino group containing preferably 2 to 30 carbon atoms, more preferably 2 to 12 carbon atoms (e.g., dimethylphosphino, diphenylphosphino). Each of these substituents may further be substituted.

A plurality of $R^1$ groups may combine with each other to form a cyclic structure. And atoms on $R^1$ groups may combine with $M^1$ to form the so-called chelate complex, or $R^1$ and $L^1$ may combine together to form a chelate ligand.

Of the groups recited above, alkyl, aryl, heteroaryl, alkoxy, aryloxy, heteroaryloxy and substituted amino groups, and groups forming phosphinine rings (phosphabenzene rings) are preferred as $R^1$ groups over the others. It is advantageous that at least one of $R^1$ groups is an alkoxy, aryloxy or heteroaryloxy group, especially an alkoxy or aryloxy group.

Further, it is appropriate that the phosphorus ligands contained in the present compound be chelate ligands.

$M^1$ represents a transition metal atom. Suitable examples of such a transition metal include ruthenium, rhodium, palladium, tungsten, rhenium, osmium, iridium and platinum. Of these metals, rhenium, iridium and platinum are preferred over the others.

$L^1$ represents a ligand. Such a ligand includes the ligands described above as ligands which the present compound can contain in addition to phosphorus ligands. As suitable examples thereof, mention may be made of halogeno ligands (preferably chlorine ligand), nitrogen-containing heterocycle ligands (such as phenylpyridine, benzoquinoline, quinolinol, bipyridyl and phenanthroline), diketone ligands (e.g., acetylacetone)), carboxylic acid ligands (e.g., acetic acid ligands), a carbon monoxide ligand, an isonitrile ligand, and a cyano ligand. Of these ligands, nitrogen-containing heterocycle ligands are preferred over the others.

$X^1$ represents a counter ion. There is, no particular limitation on such a counter ion, but it is appropriate for the counter ion to be an alkali metal ion, an alkaline earth metal ion, a halogen ion, perchlorate ion, $PF_6$ ion, or an ammonium ion (e.g., tetramethylammonium ion).

$n^1$ is preferably 3. $n^2$ is preferably 1, 2 or 3. $n^3$ is preferably 0, 1, 2 or 3. $n^4$ is preferably 0, 1, 2 or 3.

As the present compound, compounds represented by formula (2) or formula (7) (especially compounds represented by formula (2)) are advantageous over the others. As the compounds represented by formula (2), compounds represented by formula (8) are desirable, and compounds represented by formula (3) are more desirable.

As the compounds represented by formula (3), compounds represented by formulae (4), (5) and (6) respectively are preferable. In particular, the compounds represented by formula (5) are advantageous.

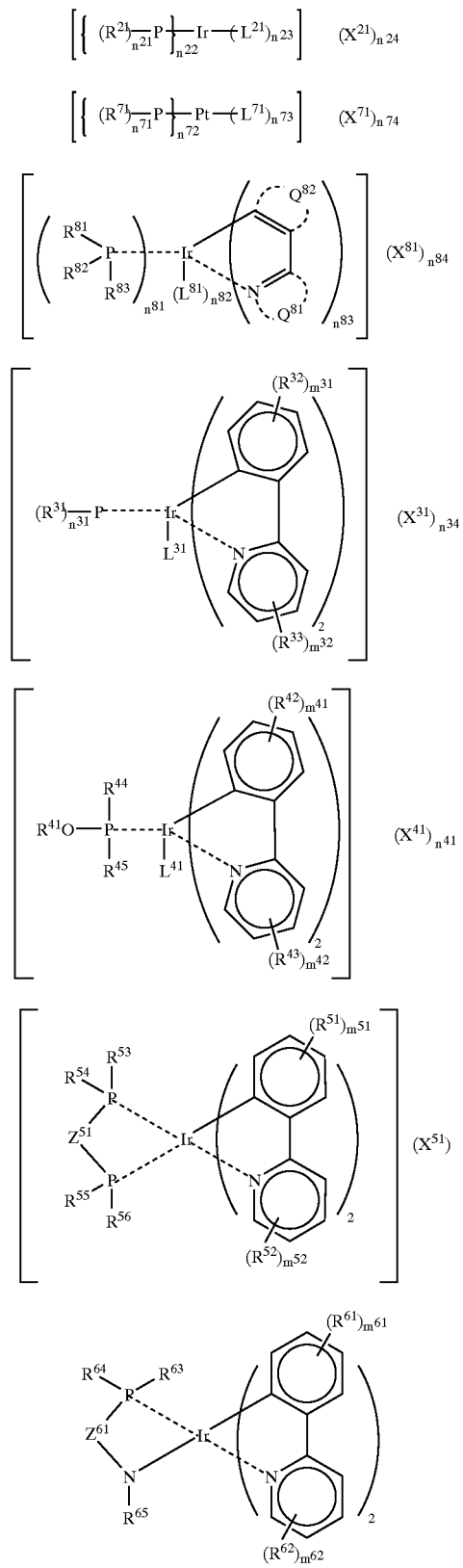

Explanations of the formula (2) are made below. $R^{21}$, $L^{21}$, $X^{21}$, $n^{21}$, $n^{22}$, $n^{23}$ and $n^{24}$ have the same meanings as $R^1$, $L^1$, $X^1$, $n^1$, $n^2$, $n^3$ and $n^4$ respectively, and each pair are also identical in preferred range.

The compounds represented by formula (2) are not particularly limited as to the valence number of iridium, but it is preferable for the iridium contained therein to be trivalent. Each of those compounds may contain one iridium atom, or may be the so-called polynuclear complex containing two or more iridium atoms (for instance, which may contain an iridium atom in $L^{21}$ or $R^{21}$). However, compounds containing one iridium atom per molecule are preferred. Although another metal atom may be contained therein in addition to the iridium atom, it is appropriate for the compound to contain an iridium atom alone.

The formula (3) is explained below. $R^{31}$, $X^{31}$ and $n^{31}$ have the same meanings as $R^1$, $X^1$ and $n^1$ respectively, and each pair are also identical in preferred range. A plurality of $R^{31}$ groups may be the same or different. $R^{32}$ and $R^{33}$ each represent a substituent, with examples including the groups recited above as those represented by $R^1$. Specifically, the groups suitable for $R^{32}$ are an alkyl group, an aryl group and a halogen atom. Of these groups, an alkyl group and a fluorine atom are preferred over the others. The groups suitable as $R^{33}$ are an alkyl group, an aryl group, an amino group and an alkoxy group. Of these groups, an alkyl group and an alkoxy groups are preferred over the others. Atoms contained in $R^{32}$ and $R^{33}$ may be bonded to the iridium atom.

$m^{31}$ and $m^{32}$ represents an integer of 0 to 4, preferably 0 to 2. When $m^{31}$ and $m^{32}$ each represent an integer more than one, $R^{32}$ groups may be the same or different and $R^{33}$ groups also may be the same or different. $n^{34}$ represents 0 or 1.

$L^{31}$ represents a monodentate ligand, or a ligand forming a chelate structure by binding with $R^{31}$. The ligands suitable as $L^{31}$ are a halogeno ligand, a ligand forming a chelate structure by binding with $R^{31}$, and a cyano ligand. Of these ligands, the ligand forming a chelate structure by binding with $R^{31}$ is preferred over the others.

$n^{34}$ represents 0 or 1. When $L^{31}$ is an anionic ligand, $n^{34}$ is 0; while, when $L^{31}$ is a nonionic ligand, $n^{34}$ is 1.

The formula (4) is explained below. $R^{41}$, $R^{42}$, $R^{43}$, $R^{44}$ and $R^{45}$ each represent a substituent. As the substituent represented by $R^{41}$, an alkyl group, an aryl group or a heteroaryl group is suitable. Examples and preferred ranges of substituents represented by $R^{44}$ and $R^{45}$ are the same as those of $R^1$. Examples and preferred ranges of substituents represented by $R^{42}$ and $R^{43}$ are the same as those of $R^{32}$ and $R^{33}$ respectively.

$L^{41}$ represents a monodentate ligand, or a ligand forming a chelate structure by binding with $R^{41}$ or $R^{45}$. The ligands preferred as $L^{41}$ are a halogen ligand, a ligand forming a chelate structure by binding with $R^{41}$ or $R^{45}$ and a cyano ligand.

$m^{41}$ and $m^{42}$ have the same meanings as $m^{31}$ and $m^{32}$ respectively, and preferred ranges thereof are the same as those of $m^{31}$ and $m^{32}$ respectively.

$n^{41}$ represents 0 or 1. When $L^{41}$ is an anionic ligand, $n^{41}$ is 0; while, when $L^{41}$ is a nonionic ligand, $n^{41}$ is 1.

The formula (5) is explained below. $R^{51}$, $R^{52}$, $R^{53}$, $R^{54}$, $R^{55}$ and $R^{56}$ each represent a substituent. Examples and preferred ranges of $R^{51}$ and $R^{52}$ are the same as those of $R^{32}$ and $R^{33}$ respectively. It is appropriate for $R^{53}$, $R^{54}$, $R^{55}$ and $R^{56}$ each to be an alkyl group, an aryl group or an alkoxy group.

$Z^{51}$ represents a linkage group. Examples of such a linkage group include an alkylene group (such as methylene, ethylene, trimethylene, propylene or tetramethylene), an alkenylene group (such as vinylene), an arylene group (such as o-phenylene, 2,3-pyridylene), an oxygen linkage, a sulfur linkage, a carbonyl linkage, a sulfonyl linkage, a sulfoxide linkage, and a linkage group having two or more of the linkage groups recited above (such as ethyleneoxy, 2,2-binaphthyl and —O(C=O)O—). These linkage groups may further have substituents. As examples of such substituents, mention may be made of the groups recited in the explanations of $R^1$. Of the linkage groups recited above as $Z^{51}$, an alkylene group, an arylene group, an oxygen linkage and a linkage group having two or more of these linkage groups are preferred over the others. In particular, it is advantageous that $Z^{51}$ is an o-phenylene group.

$X^{51}$ represents a counter anion. Examples and a preferred range of $X^{51}$ are the same as those of $X^{41}$. $m^{51}$ and $m^{52}$ each represent an integer of 0 to 4, and the preferred ranges thereof are the same as those of $m^{31}$ and $m^{32}$ respectively.

The formula (6) is explained below. $R^{61}$, $R^{62}$, $R^{63}$, $R^{64}$ and $R^{65}$ each represent a substituent. Examples and preferred ranges of $R^{61}$ and $R^{62}$ are the same as those of $R^{32}$ and $R^{33}$ respectively. It is appropriate for $R^{63}$ and $R^{64}$ each to be an alkyl group, an aryl group or an alkoxy group, and for $R^{65}$ to be an aryl group, a heteroaryl group, an acyl group, a sulfonyl group or a phosphonyl group. $Z^{61}$ represents a linkage group, and the preferred range thereof is the same as that of $Z^{51}$. $m^{61}$ and $m^{62}$ each represent an integer of 0 to 4, and the preferred ranges thereof are the same as those of $m^{31}$ and $m^{32}$ respectively.

The formula (7) is explained below. $R^{71}$, $L^{71}$, $X^{71}$ and $n^{71}$ have the same meanings as $R^1$, $L^1$, $X^1$ and $n^1$ respectively, and preferred ranges thereof are the same as those of $R^1$, $L^1$, $X^1$ and $n^1$ respectively. $n^{72}$ represents an integer of 1 to 4, preferably 1 or 2. $n^{73}$ represents an integer of 0 to 4, preferably 0 or 1. $n^{74}$ represents an integer of 0 to 2, preferably 0 or 1.

The formula (8) is explained below. $R^{81}$, $R^{82}$ and $R^{83}$ each have the same meaning as $R^1$, and a preferred range of those groups each is the same as that of $R^1$. $L^{81}$ a and $X^{81}$ have the same meanings as $L^1$ and $X^1$ respectively, and preferred ranges thereof are the same as those of $L^1$ and $X^1$ respectively. $n^{81}$ represents an integer of 1 to 4, preferably 1 or 2. $n^{82}$ represents an integer of 0 to 3, preferably 0 or 1. $n^{83}$ represents 1 or 2, preferably 2. $n^{84}$ represents 0 or 1.

$Q^{81}$ represents atoms completing a nitrogen-containing aromatic ring. $Q^{81}$ may have a substituent on the ring (as examples of such a substituent, mention may be made of the groups recited in the explanations of $R^1$). Examples of a nitrogen-containing aromatic ring completed by $Q^{81}$ include a pyridine ring, a pyrazine ring, a pyrimidine ring, a pyrazole ring, an oxazole ring, an imidazole ring, a triazole ring, an oxadiazole ring, a benzazole ring (such as a benzoxazole, benzimidazole or benzothiazole ring), and a quinoline ring. Of these rings, a pyridine ring and a benzazole ring are preferred over the others. In particular, it is advantageous that the ring completed by $Q^{81}$ is a pyridine ring.

$Q^{82}$ represents atoms completing an aromatic ring. $Q^{82}$ may have a substituent on the ring (as examples of such a substituent, mention may be made of the groups recited in the explanations of $R^1$). Examples of an aromatic ring completed by $Q^{82}$ include a benzene ring, a naphthalene ring, an anthracene ring, a phenanthrene ring, a pyridine ring, a pyrazine ring, a quinoline ring, a thiophene ring, and a furan ring. Of these rings, a benzene ring, a pyridine ring, a pyrazine ring and a thiophene ring are preferred over the others. In particular, it is advantageous that the ring completed by $Q^{82}$ is a benzene ring.

The present compound may be a low molecular weight compound, or an oligomer or polymer compound containing repeating units represented by formula (1) in the main chain and/or side chains (suitable mass-average molecular weight (on a polystyrene basis) of which is in the range of 1,000 to 5,000,000, preferably 2,000 to 1,000,000, particularly preferably 3,000 to 100,000). It is advantageous that the present compound is a low molecular weight compound.

Examples of the present compound are illustrated below, but it should be understood that these examples are not to be construed as limiting the scope of the invention in any way.

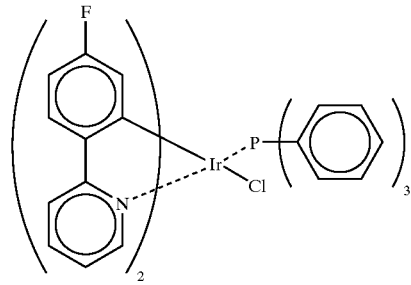

(1-1)

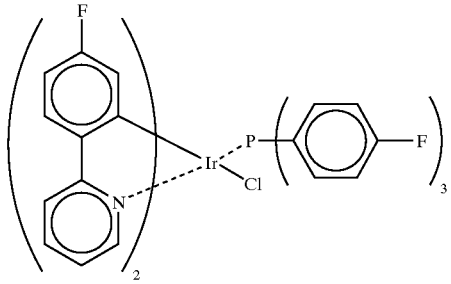

(1-2)

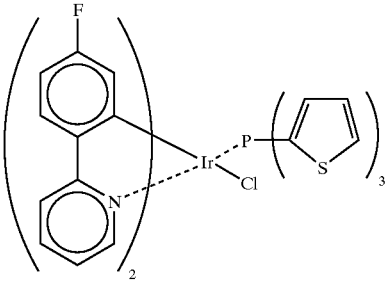

(1-3)

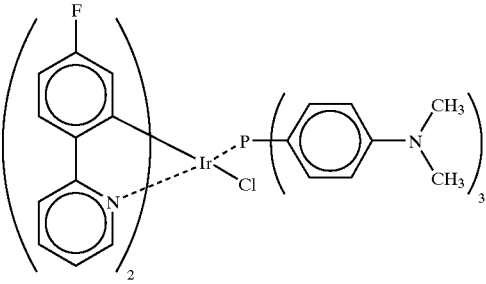

(1-4)

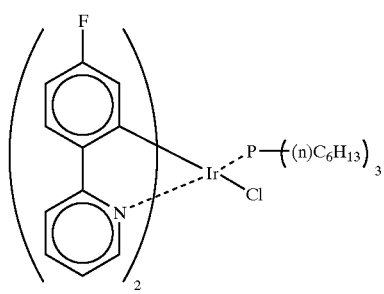
(1-5)
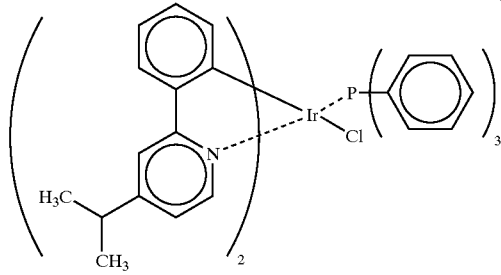
(1-10)
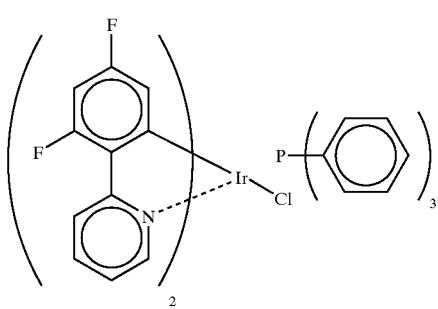
(1-6)
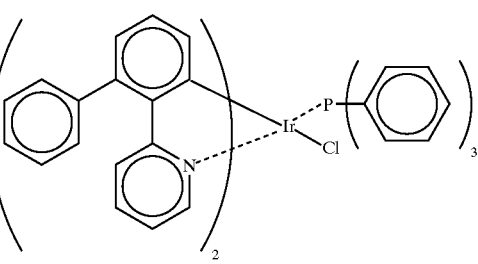
(1-11)
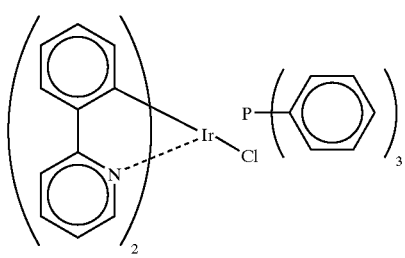
(1-7)
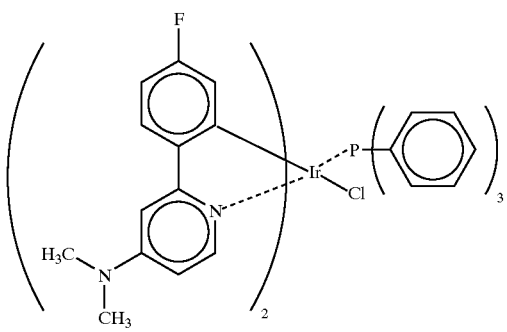
(1-12)
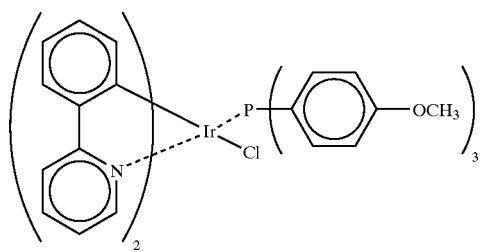
(1-8)
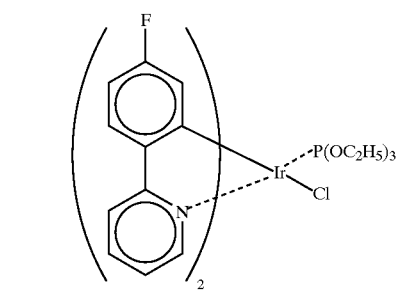
(1-13)
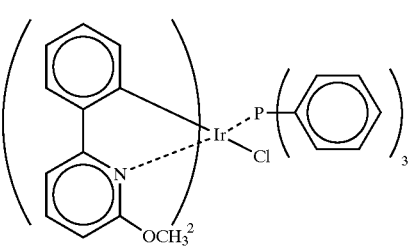
(1-9)
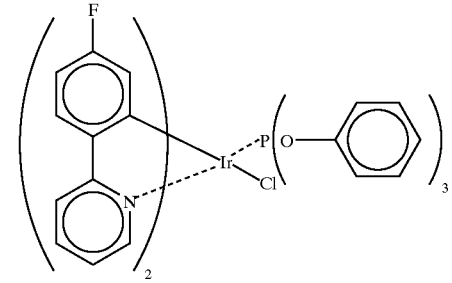
(1-14)

(1-15)
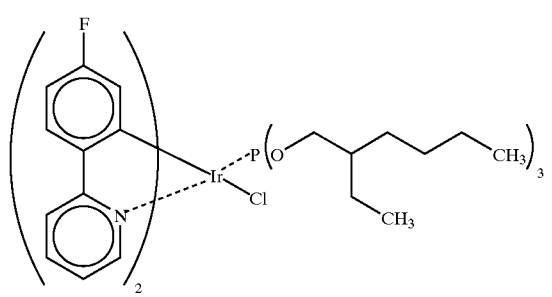
(1-16)
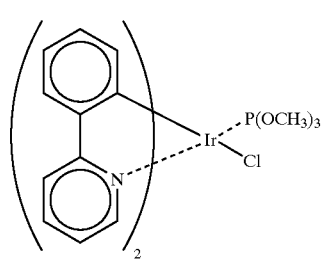
(1-17)
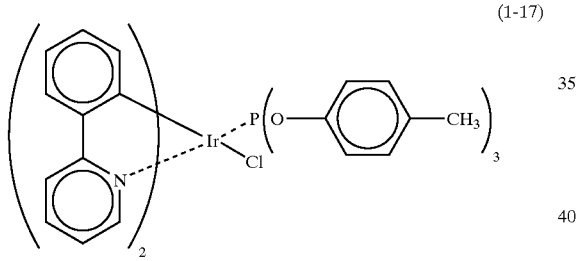
(1-18)
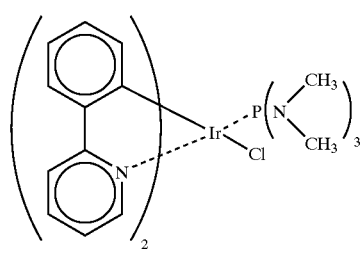
(1-19)
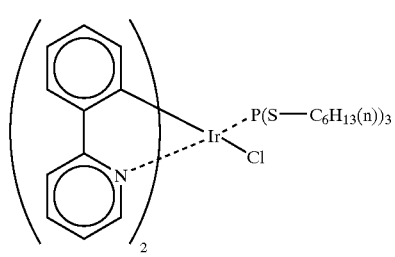
(1-20)
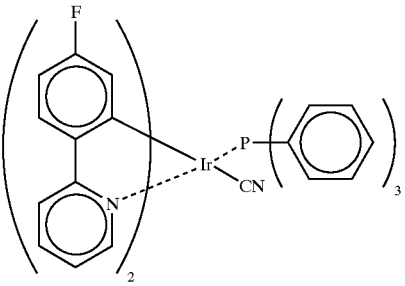
(1-21)
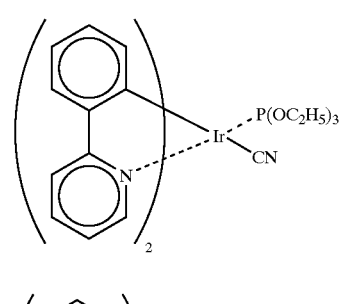
(1-22)
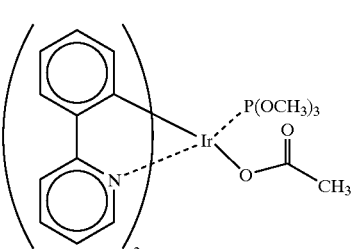
(1-23)
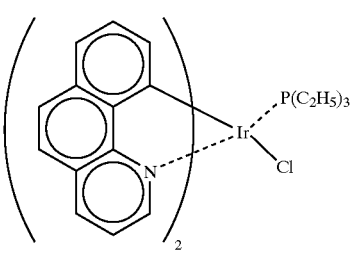
(1-24)
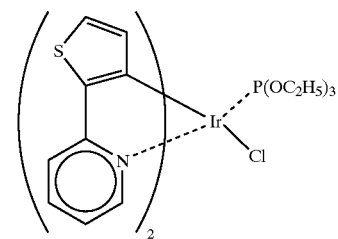
(1-25)
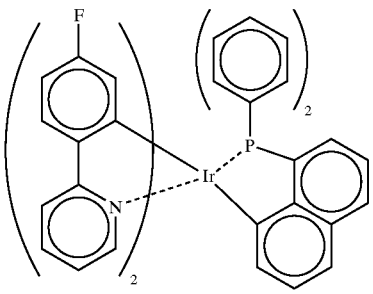

(1-26)
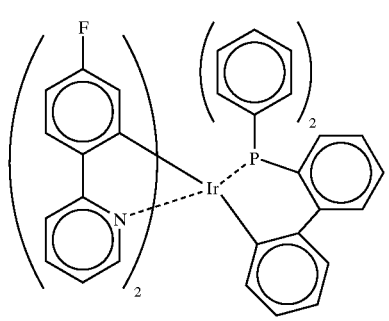
(1-27)
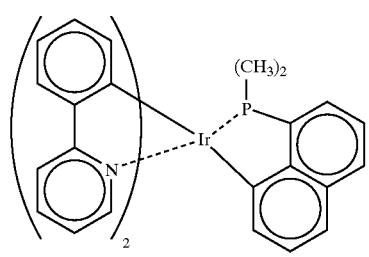
(1-28)
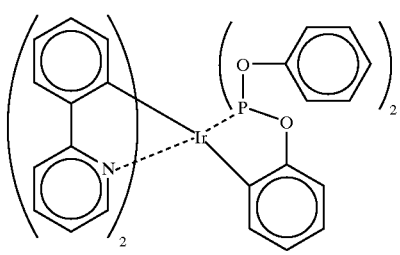
(1-29)
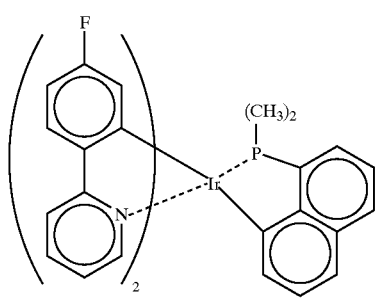
(1-30)
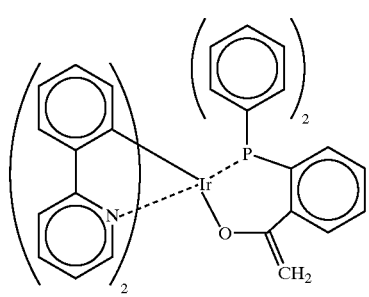
(1-31)
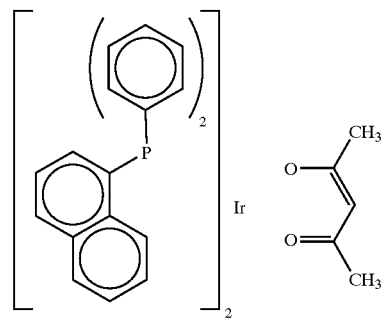
(1-32)
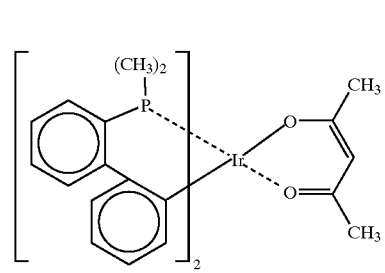
(1-33)
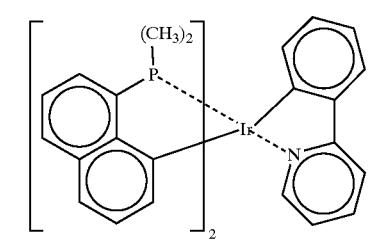
(1-34)
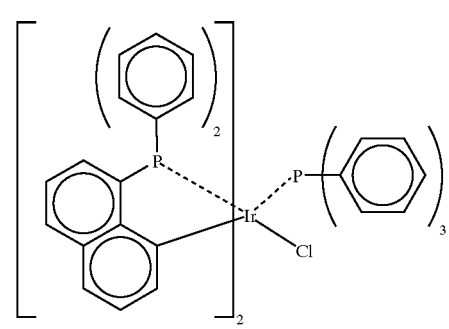
(1-35)
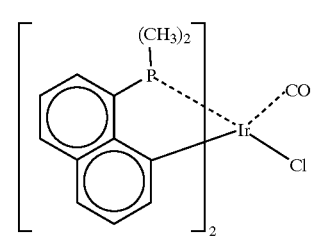

(1-36) 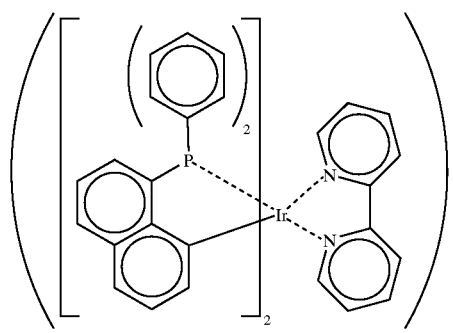
(1-41) 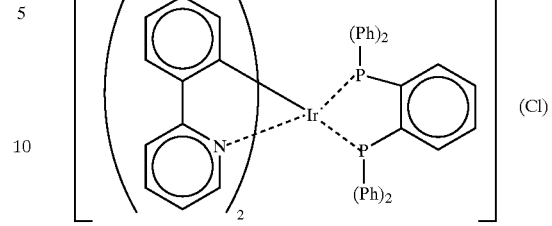
(1-37) 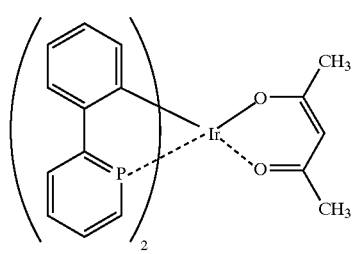
(1-42) 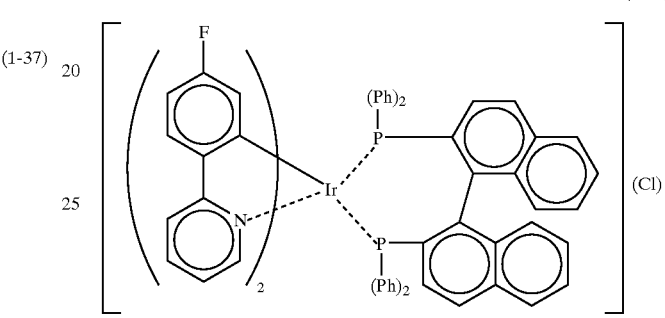
(1-38) 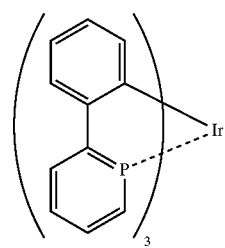
(1-43) 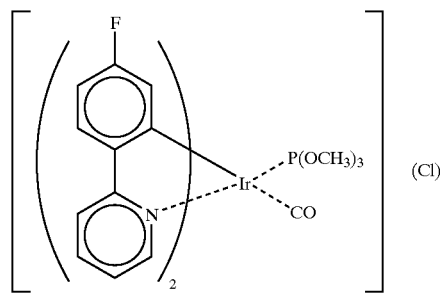
(1-39) 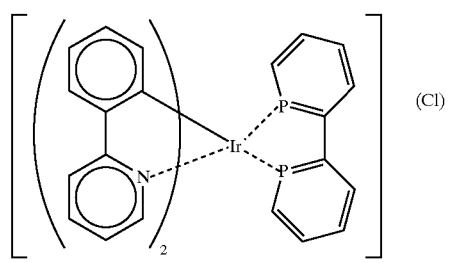
(1-44) 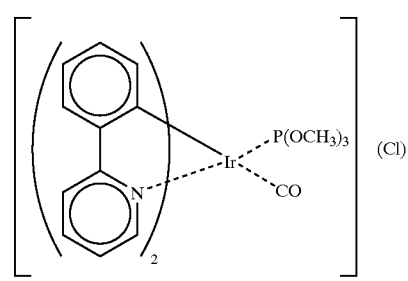
(1-40) 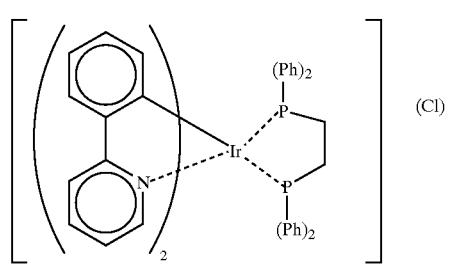
(1-45) 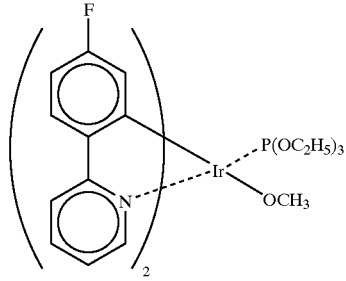

(1-46)
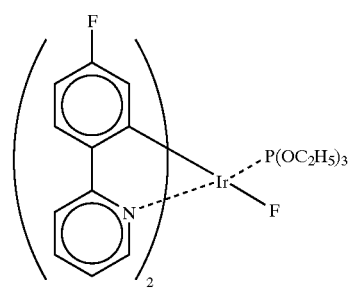
(1-47)
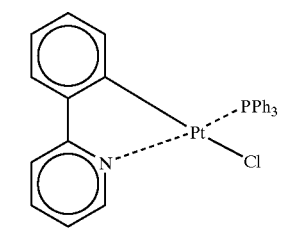
(1-48)
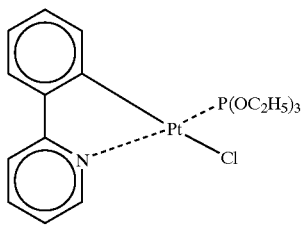
(1-49)
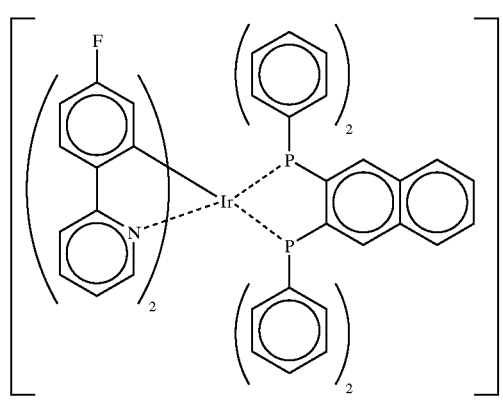
(1-50)
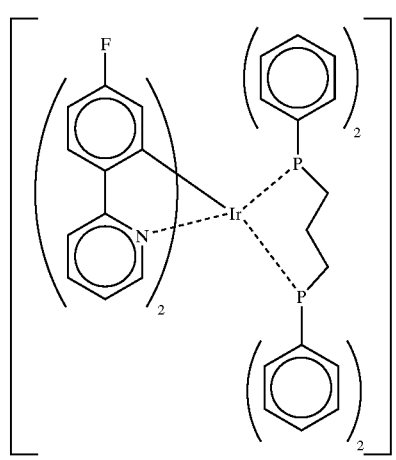
(1-51)
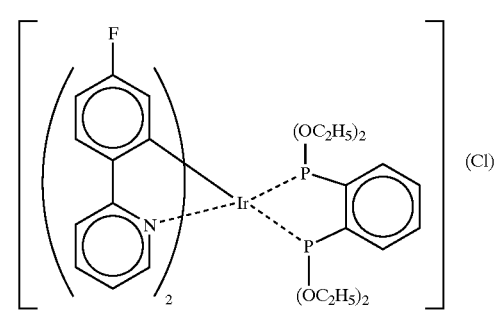
(1-52)
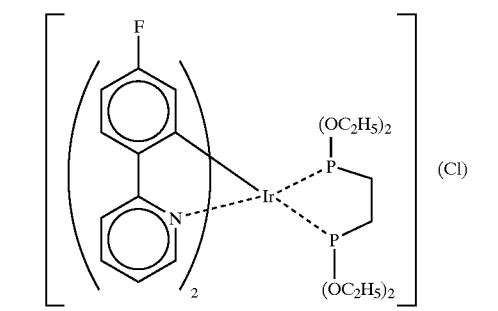
(1-53)
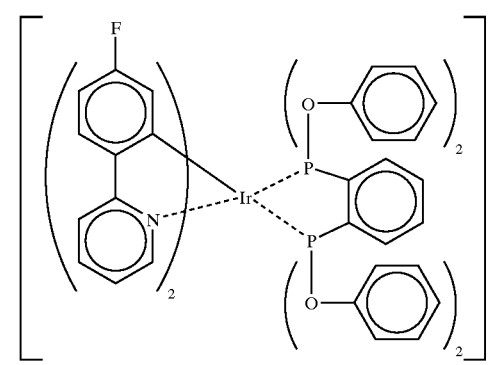
(1-54)
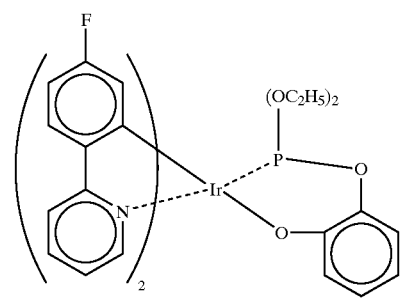
(1-55)
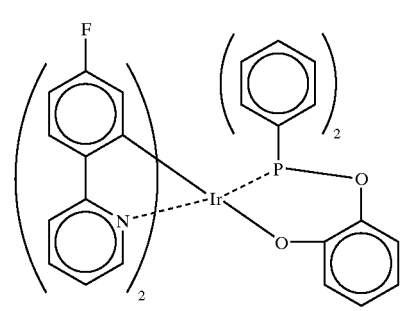

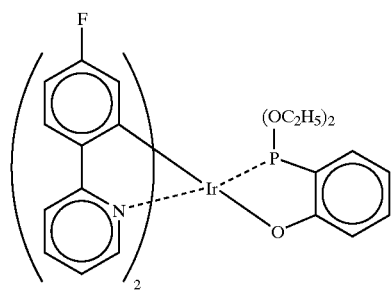 (1-56)
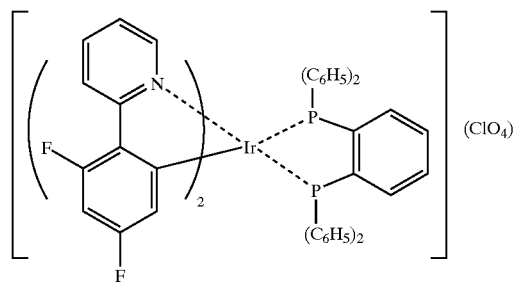 (1-61)
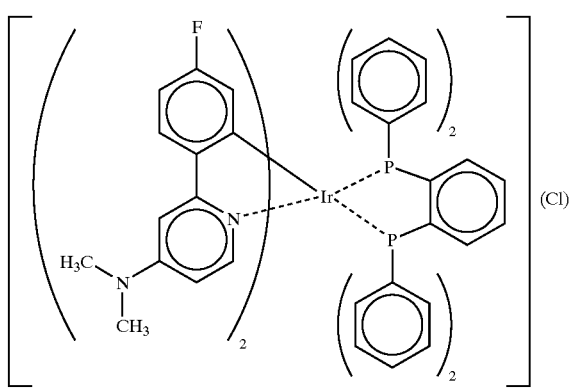 (1-57)
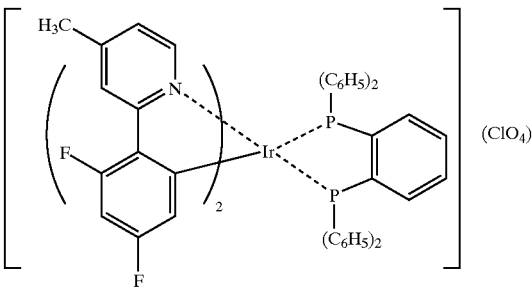 (1-62)
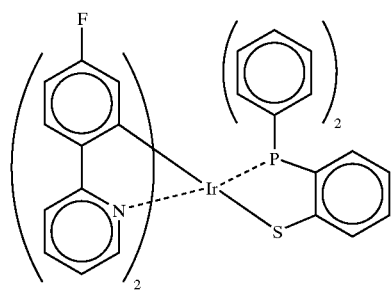 (1-58)
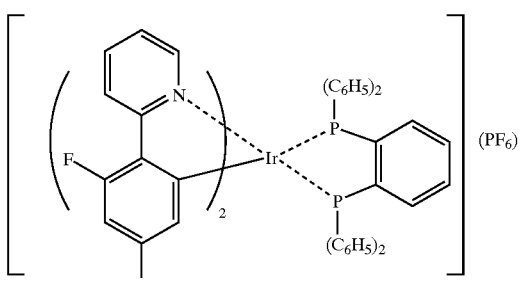 (1-63)
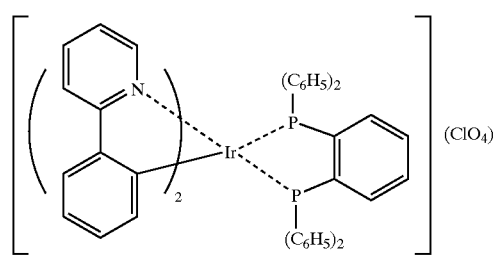 (1-59)
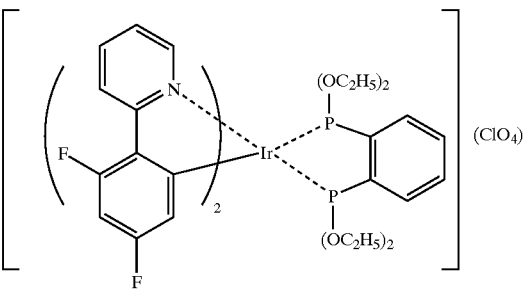 (1-64)
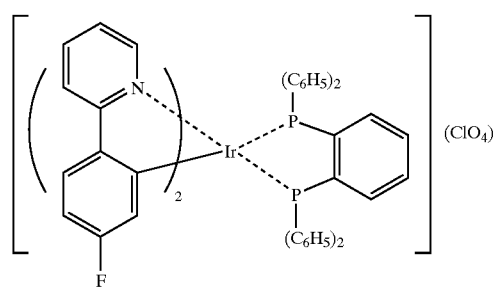 (1-60)
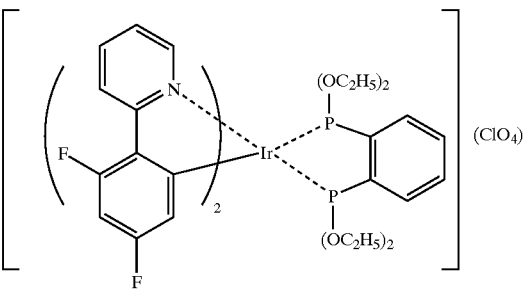 (1-65)

(1-66)
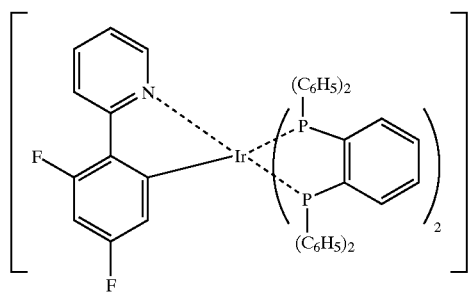
(1-67)
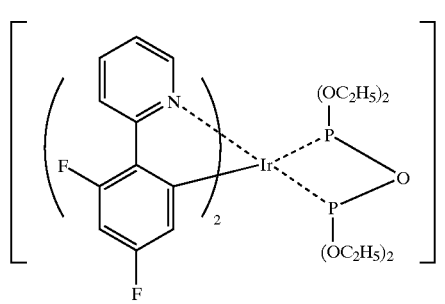
(1-68)
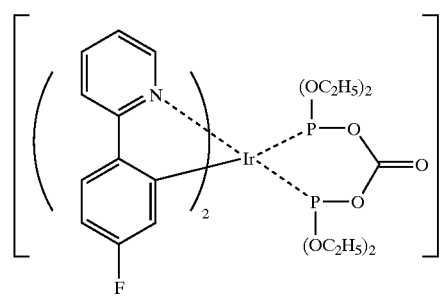
(1-69)
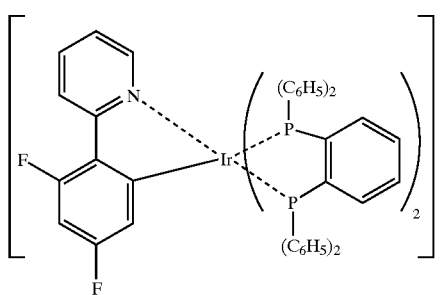
(1-70)
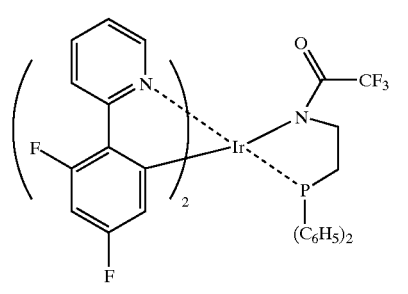
(1-71)
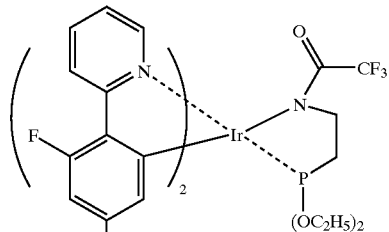
(1-72)
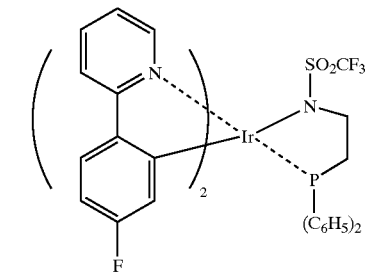
(1-73)
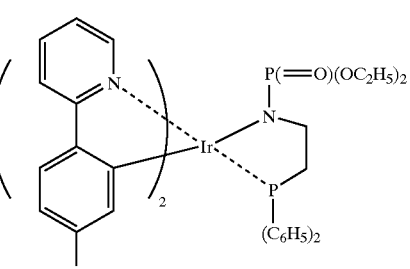
(1-74)
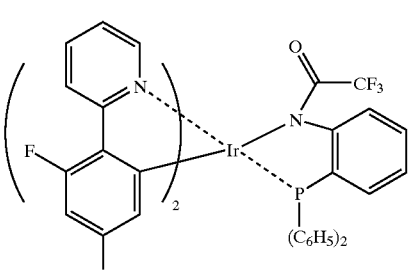
(1-75)
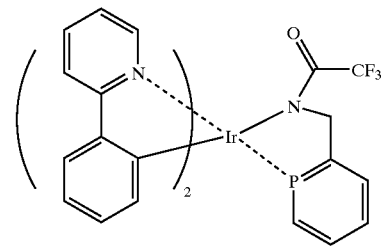
(1-76)
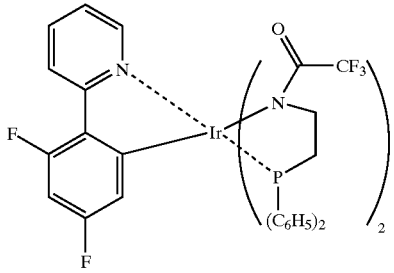

-continued (1-77)
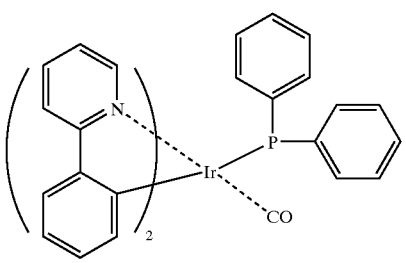

(1-78)
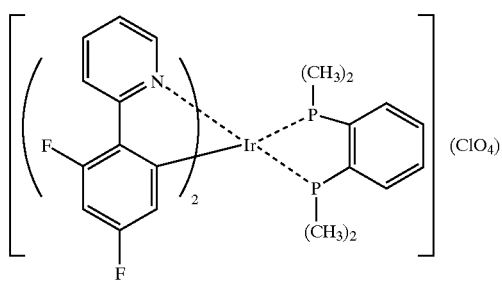
(ClO₄)

(1-79)
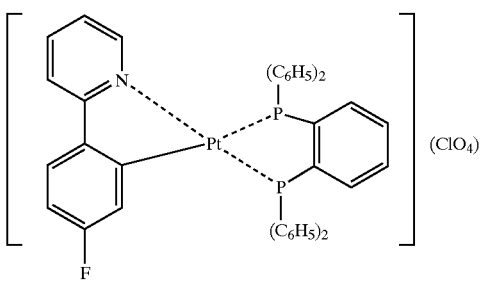
(ClO₄)

(1-80)
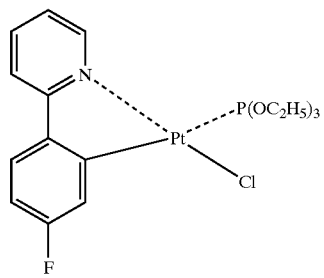

(1-81)
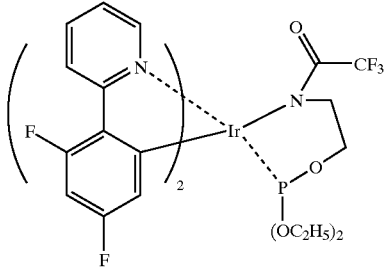

The compounds according to the invention can be synthesized using various methods. For instance, they each can be obtained by mixing phosphorus ligand(s) and various other ligands, or these ligands in dissociated states, with a transition metal compound, wherein a solvent (such as a halogen-containing solvent, an alcoholic solvent, an ether solvent or water) may be present or absent, a base (with examples including various inorganic and organic bases, such as sodium methoxide, potassium t-butoxide, triethylamine and potassium carbonate) may be present or absent and the temperature may be kept below room temperature or raised by heating in a usual way, by microwave heating, or the like.

Next, descriptions of light-emitting devices containing the present compounds are provided. To light-emitting devices according to the invention, it does not much matter what system, operation method and utilization mode are adopted so long as the devices use the present compounds. However, the present devices prefer to utilize luminescence from the present compounds or to use the present compounds as electron transport materials. As typical examples of a light-emitting device, mention may be made of organic EL (electroluminescence) devices.

In the light-emitting device according to the invention, the light-emitting layer preferably comprises the present compound, that is a guest compound, doped into a host compound (a guest compound corresponds to a compound having a transition metal atom-phosphorus atom bond). $T_1$ level (the energy level of the lowest excited triplet state) of the host compound is preferably higher than that of the guest compound. $T_1$ level of the host compound is preferably from 260 kJ/mol to 356 kJ/mol (from 62 kcal/mol to 85 kcal/mol), more preferably, from 272 kJ/mol to 335 kJ/mol (from 65 kcal/mol to 80 kcal/mol).

$T_1$ level of a compound, which is included in a layer being contact with the light-emitting layer such as a hole transport layer, an electron transporting layer, a hole blocking layer and the like, is preferably higher than that of the guest compound included in the light-emitting layer. $T_1$ level of the compound included in a layer being contact with the light-emitting layer is preferably from 260 kJ/mol to 356 kJ/mol (from 62 kcal/mol to 85 kcal/mol), more preferably, from 272 kJ/mol to 335 kJ/mol (from 65 kcal/mol to 80 kcal/mol). As the compound which meets above described range of $T_1$ level, the compounds disclosed in Japanese Patent application No. 2001-197135 and 2001-76704 is suitably used. The preferable range of the compound is also disclosed in Japanese Patent application No. 2001-197135 and 2001-76704.

The organic layers of the light-emitting devices containing the present compounds are not particularly limited in their formation methods, but they can be formed using, e.g., a resistance heating vapor deposition method, an electron beam method, a sputtering method, a molecular lamination method, a coating method, an inkjet method, a printing method or a transfer method. Of these methods, the resistance heating vapor deposition method and the coating method are preferred in the characteristic and manufacturing aspects.

Every light-emitting device according to the invention is a device comprising a pair of electrodes, namely an anode and a cathode, and a light-emitting layer or at least two thin layers (films) of organic compounds, inclusive of a light-emitting layer, sandwiched between the electrodes. The thin layers the device may have in addition to the light-emitting layer are, e.g., a hole injection layer, a hole transport layer, an electron injection layer, an electron transport layer and a protective layer. Each of these layers may have another function. For forming each of those layers, various materials can be employed.

The anode supplies holes to a hole injection layer, a hole transport layer and a light-emitting layer. As anode materials, metals, alloys, metal oxides, electrically conductive materials and mixtures thereof, preferably materials having a work function of at least 4 eV, can be used.

Examples of such materials include electrically conductive metal oxides, such as tin oxide, zinc oxide, indium oxide and indium tin oxide (ITO), metals such as gold, silver, chromium and nickel, mixtures or laminates of those metals and electrically conductive metal oxides, electrically conductive inorganic materials such as copper iodide and copper sulfide, electrically conductive organic materials such as polyaniline, polythiophene and polypyrrole, and laminates of those electrically conductive materials and ITO. Of the materials recited above, the electrically conductive metal oxides are preferred. In particular, ITO is advantageous over the others from the viewpoints of productivity, conductivity and transparency. The suitable thickness of the anode, though can be selected depending on the anode material, is generally from 10 nm to 5 μm, preferably 50 nm to 1 μm, particularly preferably 100 nm to 500 nm.

In general the anode is used in the state of a layer formed on a soda lime glass, alkali-free glass or transparent resin substrate. In the case of using a glass substrate, alkali-free glass is preferred from the viewpoint of reduction in ions eluted from the glass. When soda lime glass is used for the substrate, it is appropriate that a barrier coat of silica be provided on the glass substrate. The substrate thickness has no particular limitation so long as the substrate can ensure mechanical strength for the anode. For instance, the suitable thickness of a glass substrate is at least 0.2 mm, preferably at least 0.7 mm.

The methods suitable for making the anode vary with the material used. In the case of ITO, for instance, the film formation can be carried out using an electron beam method, a sputtering method, a resistance heating vapor deposition method, a chemical reaction method (e.g., sol-gel method) or the method of coating a dispersion of indium tin oxide.

Washing and other treatments for the anode enable the device to get a reduction in operation potential and elevation of light-emitting efficiency. In the case of an anode using ITO, it is effective for the anode to receive UV-ozone treatment or plasma treatment.

The cathode supplies electrons to an electron injection layer, an electron transport layer and a light-emitting layer. In selecting the cathode, the adhesion to a layer adjacent to the cathode, such as an electron injection layer, an electron transport layer or a light-emitting layer, the ionization potential and the stability are taken into consideration. As cathode materials, metals, alloys, metal halides, metal oxides, electrically conductive materials and mixtures thereof can be employed. Examples of such materials include alkali metals (e.g., Li, Na, K) and the fluorides or oxides thereof, alkaline earth metals (e.g., Mg, Ca) and the fluorides or oxides thereof, gold, silver, lead, aluminum, Na—K alloy or mixture, Li—Al alloy or mixture, Mg—Ag alloy or mixture, and rare earth metals such as indium and ytterbium. Of these materials, the materials having a work function of at most 4 eV are preferred over the others. In particular, aluminum, Li—Al alloy or mixture and Mg—Ag alloy or mixture are used to advantage. The cathode may have a single-layer structure formed of the compound or mixture as recited above or a lamination structure comprising the compounds or/and mixtures as recited above. For instance, an Al/LiF lamination structure and an Al/Li$_2$O lamination structure are appropriate for the cathode. The suitable thickness of the cathode, though can be chosen depending on the cathode material, is generally from 10 nm to 5 μm, preferably 50 nm to 1 μm, particularly preferably 100 nm to 1 μm.

In making the cathode, various known methods, such as an electron beam method, a sputtering method, a resistance heating vapor deposition method and a coating method, can be adopted. The metals as recited above may be evaporated independently, or two or more thereof may be evaporated simultaneously. Further, it is possible to evaporate a plurality of metals at the same time to form an alloy electrode, or the previously prepared alloy may be subjected to vapor deposition.

It is appropriate for the light-emitting device that both anode and cathode have low sheet resistance, specifically several hundreds Ω/square at the highest.

For a light-emitting layer, any materials can be used so long as they can form a layer having the following functions. One function is to receive hole injection from the anode, the hole injection layer or the hole transport layer as well as electron injection from the cathode, the electron injection layer or the electron transport layer when the electric field is applied to the light-emitting device. Another function is to permit the charges injected in the layer to move. The other function is to enable the emission of light by providing a place for recombining holes and electrons. Further, it does not matter to materials used for the light-emitting layer whether luminescence is produced from singlet-state excitons or triplet-state excitons so long as they can produce luminescence. Examples of such materials include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyraridine derivatives, cyclopentadiene derivatives, bisstyrylanthracene derivatives, quinacridone derivatives, pyrrolopyridine derivatives, thiadiazolopyridine derivatives, styrylamine derivatives, aromatic dimethylidyne derivatives, various metal complexes represented by metal or rare earth complexes of 8-quinolinol derivatives, polymeric compounds such as polythiophene, polyphenylene and polyphenylenevinylene, organosilane derivatives, and the present compounds. Although the light-emitting layer has no particular restrictions as to the thickness, the suitable thickness thereof is generally from 1 nm to 5 μm, preferably 5 nm to 1 μm, particularly preferably 10 nm to 500 nm.

The suitable proportion of the present compound in the light-emitting layer is from 0.1 to 100%, preferably from 1 to 50%, particularly preferably from 5 to 30%, to the total mass of the light-emitting layer.

The light-emitting layer may be formed of a single compound or a plurality of compounds. And the light-emitting layer may be constituted of one layer or two or more layers. In the latter case, the light-emitting layer may be designed so that the constituent layers thereof radiate differently colored beams respectively, thereby producing, e.g., white luminescence. In the former case also, the light-emitting layer may produce white luminescence. Further, each of the layers constituting the light-emitting layer may be formed of a single material or more than one compound.

As to the method of forming the light-emitting layer, there is no particular restriction, but various methods can be adopted. For instance, a resistance heating vapor deposition method, an electron beam method, a sputtering method, a molecular lamination method, a coating method (e.g., a spin coating, cast coating or dip coating method), an ink jet method, a printing method, an LB method and a transfer method are usable herein. Of these methods, a resistance heating vapor deposition method and a coating method are preferred over the others.

The materials for a hole injection layer and a hole transport layer may be any materials so long as they have any one of the functions as an injector of holes from the anode, a transporter of holes and a barrier against electrons injected from the cathode. Examples of materials hitherto known to have one of such functions include carbazole derivatives, triazole derivatives, oxazole derivatives, oxadiazole derivatives, imidazole derivatives, polyarylalkane derivatives, pyrazoline derivatives pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, electrically conductive polymers and oligomers such as poly(N-vinylcarbazole) derivatives, aniline copolymers, thiophene oligomers and polythiophene, organic silane compounds, carbon film, and the present compounds. The suitable thickness of the hole injection layer and the hole transport layer each, though it has no particular limitation, is generally from 1 nm to 5 μm, preferably 5 nm to 1 μm, particularly preferably 10 nm to 500 nm. Each of the hole injection layer and the hole transport layer may have a single-layer structure constituted of one or more of the materials recited above or a multiple-layer structure made up of at least two layers having the same composition or different compositions.

As a method for forming the hole injection layer and the hole transport layer, a vacuum evaporation method, an LB method, a method of coating solutions or dispersions of hole-injecting and transporting agents (by the use of, e.g., a spin coating, cast coating or dip coating method), an inkjet method, a printing method or a transfer method can be adopted. When the coating method is adopted, the agents to constitute those layers may be dissolved or dispersed in a coating solvent, together with a resinous ingredient. Examples of such a resinous ingredient include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, polyvinyl acetate, ABS resin, polyurethane, melamine resin, unsaturated polyester resin, alkyd resin, epoxy resin and silicone resin.

The materials for the electron injection layer and the electron transport layer may be any materials so long as they have any one of the functions as an injector of the electrons from the cathode, a transporter of electrons and a barrier against holes injected from the anode. Examples of materials known to have such functions include triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodimide derivatives, fluorenylidenemethane derivatives, distyrylpyrazine derivatives, tetracarboxylic acid anhydrides of aromatic condensed rings such as naphthalene and perylene, phthalocyanine derivatives, various metal complexes represented by metal complexes of 8-quinolinol derivatives, metallophthalocyanines and metal complexes having benzoxazole or benzothiazole ligands, organosilane derivatives and the present compounds. The suitable thickness of the electron injection layer and the electron transport layer each, though it has no particular limitation, is generally from 1 nm to 5 μm, preferably 5 nm to 1 μm, particularly preferably 10 nm to 500 nm. Each of the electron injection layer and the electron transport layer may have a single-layer structure constituted of one or more of the materials as recited above, or a multiple-layer structure made up of at least two layers having the same composition or different compositions.

As a method of forming the electron injection layer and the electron transport layer, a vacuum evaporation method, an LB method, a method of coating solutions or dispersions of electron-injecting and transporting agents as recited above (by the use of, e.g., a spin coating, cast coating or dip coating method), an ink jet method, a printing method or a transfer method can be adopted. In the case of adopting a coating method, the electron-injecting and transporting agents can be dissolved or dispersed together with a resinous ingredient. Examples of a resinous ingredient usable therein include the same resins as employed for the hole injection and transport layers.

The materials for a protective layer may be any substances so long as they have a function capable of inhibiting the invasion of a device deterioration promoter, such as moisture or oxygen, into the device. Examples of such a substance include metals such as In, Sn, Pb, Au, Cu, Ag, Al, Ti and Ni, metal oxides such as MgO, SiO, $SiO_2$, $Al_2O_3$, GeO, NiO, CaO, BaO, $Fe_2O_3$, $Y_2O_3$ and $TiO_2$, metal nitrides such as $SiN_x$ and $SiN_xO_y$, metal fluorides such as $MgF_2$, LiF, $AlF_3$ and $CaF_2$, polyethylene, polypropylene, polymethyl methacrylate, polyimide, polyurea, polytetrafluoroethylene, polychlorotrifluoroethylene, polydichlorodifluoroethylene, copolymer of chlorotrifluoroethylene and dichlorodifluoroethylene, a copolymer prepared by polymerizing a mixture of tetrafluoroethylene and at least one comonomer, fluorine-containing copolymers having cyclic structures on the main chain, a water-absorbing substance having a water absorption rate of at least 1%, and a moisture-proof substance having a water absorption rate of at most 0.1%.

The protective layer also has no particular restriction as to the formation method, but any of a vacuum evaporation method, a sputtering method, a reactive sputtering method, a molecular beam epitaxy (MBE) method, a cluster ion beam method, an ion plating method, a plasma polymerization method (high frequency excitation ion plating method), a plasma chemical vapor deposition (CVD) method, a laser CVD method, a heat CVD method, a gas source CVD method, a coating method, a printing method and a transfer method can be adopted for the formation thereof.

EXAMPLE

The present invention will now be illustrated in more detail by reference to the following examples. However, embodiments of the invention should not be construed as being limited to these examples.

Synthesis of Compound (1-1)

Chloroform in an amount of 20 ml was added to 0.2 g of an iridium complex "a" (prepared referring to the method described in *J. Am. Chem. Soc.*, 1984, 106, 6647) and 0.17 g of triphenyl phosphine, and stirred under reflux for 3 hours. After cooling to room temperature, the reaction solution was purified by column chromatography on silica gel (developing solvent:chloroform) to yield 0.1 g of a pale yellow solid (1-1). After it was de-aerated, the solid (1-1) (solvent: toluene, concentration: $5.0 \times 10^{-6}$ M) was examined for luminescence, and the luminescence produced thereby was found to have λmax at 470 nm. Although the iridium complex "a" was examined for luminescence under the same condition as the solid (1-1), no luminescence was observed.

Synthesis of Compound (1-13)

Chloroform in an amount of 20 ml was added to 0.2 g of an iridium complex "a" and 0.12 ml of triethyl phosphite, and stirred under reflux for 3 hours. After cooling to room temperature, the reaction solution was purified by column chromatography on silica gel (developing solvent: chloroform) to yield 0.13 g of a pale yellow solid (1-13). After it was de-aerated, the solid (1-13) (solvent: toluene, concentration: $5.0 \times 10^{-6}$ M) was examined for luminescence, and the luminescence produced thereby was found to have λmax at 465 nm.

Synthesis of Compound (1-61)

Chloroform in an amount of 20 ml was added to 1.0 g of an iridium complex "b" (prepared referring to the method described in *J. Am. Chem. Soc.*, 1984, 106, 6647) and 1.2 g of a phosphine ligand "c", and stirred under reflux for 3 hours. After cooling to room temperature, the reaction solution was purified by column chromatography on silica gel (wherein the chromatogram was developed using chloroform first and then a chloroform-methanol mixture) to yield 0.8 g of a pale yellow solid. To this solid were added sequentially 30 ml of methanol and 0.5 g of $NaClO_4 \cdot H_2O$.

The thus deposited solid was filtered off, and then washed with methanol. The resulting solid was recrystallized from a chloroform-hexane mixture to yield 0.5 g of a white solid (1-61). The structure of the white solid was confirmed by NMR. After it was de-aerated, the solid (1-61) (solvent: toluene, concentration: $5.0 \times 10^{-6}$ M) was examined for phosphorescence, and the phosphorescence produced thereby was found to have λmax at 440 nm. The quantum yield ϕ of this phosphorescence was 60%.

Synthesis of Compound (1-70)

Chloroform in an amount of 10 ml was added to 0.2 g of an iridium complex "b" and 0.17 g of a phosphine ligand "d". To this solution, 0.1 ml of a methanol solution of sodium methoxide (28 mass %) was further added. The resulting admixture was stirred under reflux for 3 hours. After cooling to room temperature, the reaction solution was purified by column chromatography on silica gel (wherein the chromatogram was developed using chloroform first and then a chloroform-methanol mixture) to yield 0.1 g of a yellow solid (1-70). The structure of the yellow solid (1-70) was confirmed by measurement with a mass spectrometer.

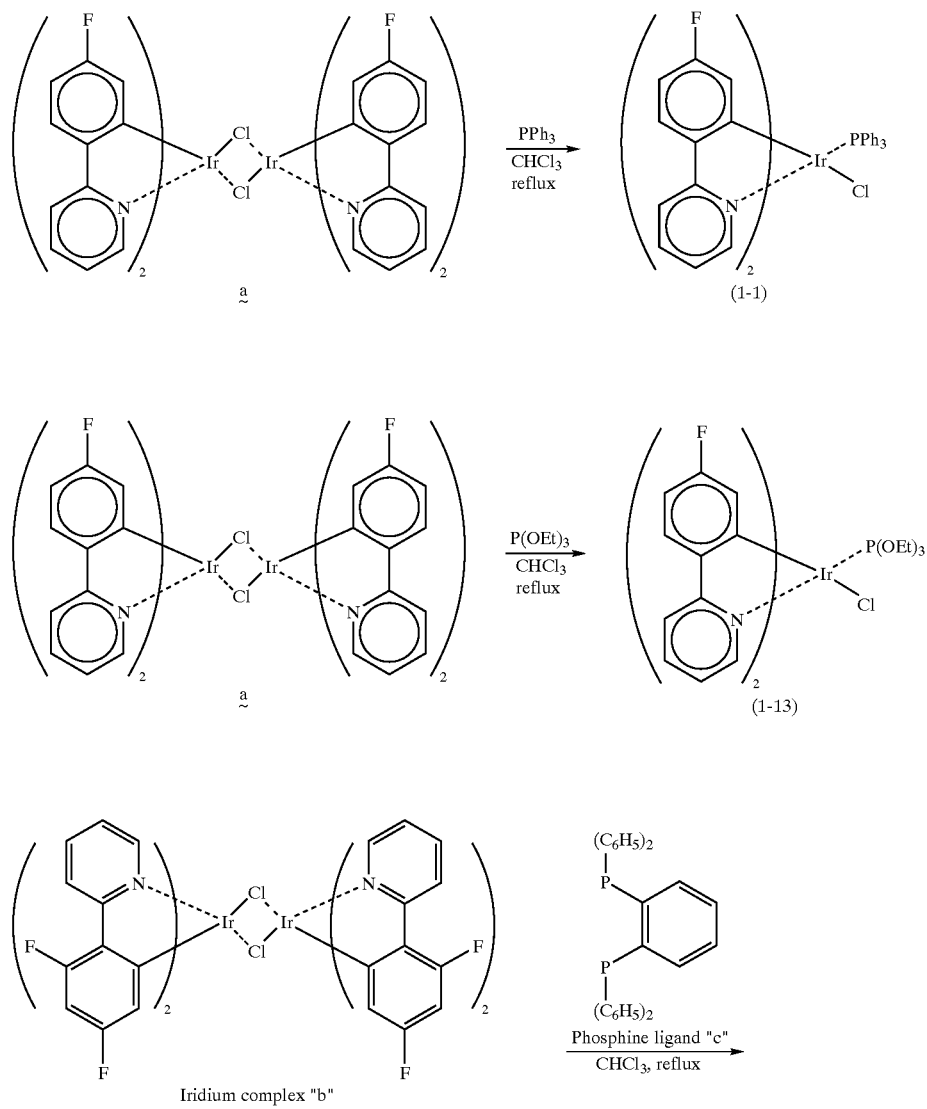

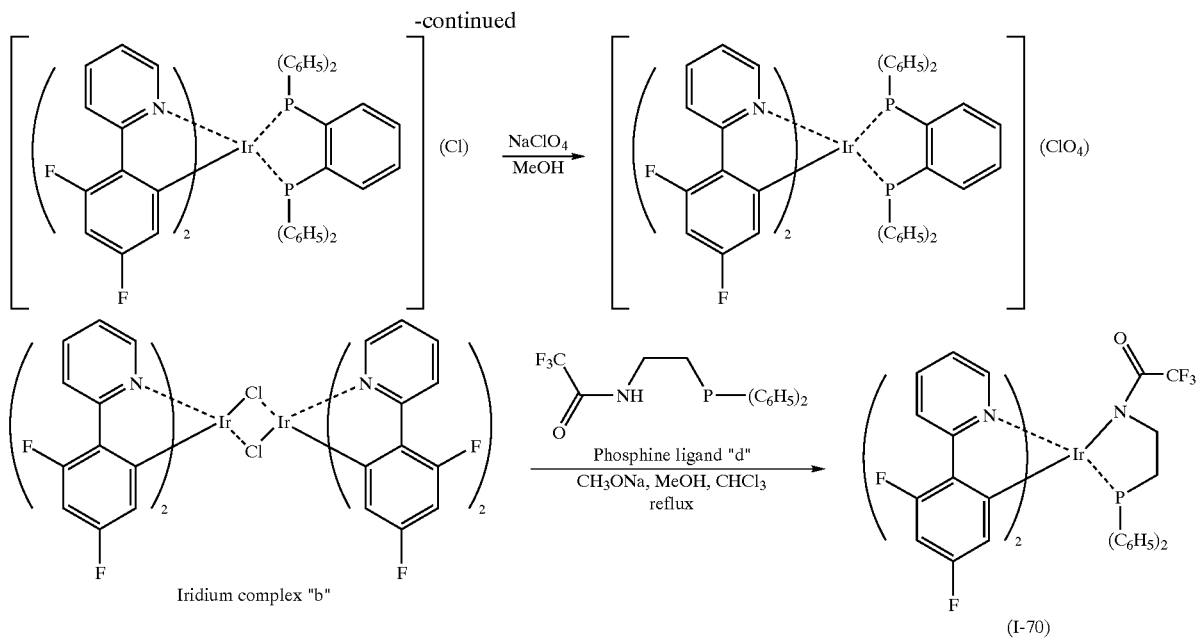

Comparative Example 1

Poly(N-vinylcarbazole) in an amount of 40 mg, 12 mg of PBD [2-(4-biphenyl)-5-(4-t-butylphenyl)-1,3,4-oxadiazole] and 1 mg of compound (A) were dissolved in 2.5 ml of dichloroethane, and spin-coated on a cleaned substrate (at 1,500 r.p.m. for 20 seconds). The thickness of the thus formed organic layer was 98 nm. A patterned mask (for adjusting each emission area to 4 mm×5 mm) was put on the thin organic layer, and installed in a vacuum evaporation apparatus. By the use of this apparatus, Mg and Ag were deposited simultaneously on the thin organic layer via the patterned mask in a Mg/Ag ratio of 10/1, thereby forming a metallic film having a thickness of 50 nm. On this metallic film, Ag was further deposited into a 50 nm-thick film. The thus produced EL device was made to luminesce by applying thereto a DC constant voltage by means of a source measure unit, Model 2400, made by Toyo Technica Co., Ltd., and examined for luminance and wavelengths of luminescence by using a luminometer BM-8 made by Topcon Co. and a spectrum analyzer PMA-11 made by Hamamatsu Photonics Co. respectively. The luminescence thus produced had a green color, an ELmax value of 505 nm and a CIE chromaticity (x,y) value of (0.27, 0.57).

Compound (A)

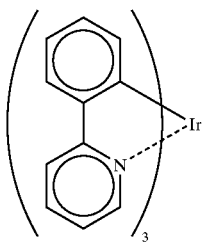

Compound (B)

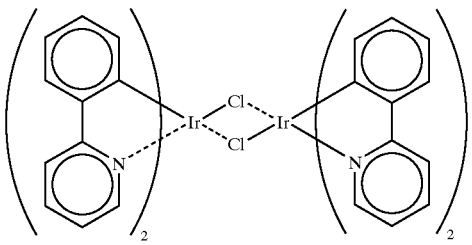

Comparative Example 2

A device was produced and evaluated in the same manner as in Comparative Example 1, except that Compound (B) was used in place of Compound (A). As a result, no luminescence was produced from the device.

Example 1

A device was produced in the same manner as in Comparative Example 1, except that the present Compound (1-13) was used in place of Compound (A). As a result, blue luminescence having an ELmax value of 475 nm was obtained.

Example 2

On a cleaned substrate, Baytron P[a PEDOT-PSS solution (polydioxyethylenethienylene-polystyrenesulfonic acid doped material), a product of Bayer A.G.] was spin-coated (at 1,000 r.p.m. for 30 seconds) and dried at 150° C. under vacuum for 1.5 hours. The thus formed organic layer had a thickness of 70 nm. On this layer was spin-coated (at 1,000 r.p.m. for 20 seconds) a solution containing 10 mg of polymethyl methacrylate, 20 mg of Compound C and 1 mg of the present Compound (1-61) in 2 ml of dichloroethane. The resulting substrate was installed in a vacuum evaporation apparatus, and thereon a 36 nm-thick film of Compound D was formed by evaporation. On the thus formed organic thin layer, a patterned mask (for adjusting each emission area to 4 mm×5 mm) was put, and thereon were formed a 3 nm-thick lithium fluoride film first and then a 400 nm-thick aluminum film by evaporation. The thus produced EL device was made to luminesce by applying thereto a DC constant voltage by means of a source measure unit, Model 2400, made by Toyo Technica Co., Ltd., and examined for luminance and wavelengths of luminescence by using a luminometer BM-8 made by Topcon Co. and a spectrum analyzer PMA-11 made by Hamamatsu Photonics Co. respectively. The luminescence thus produced had a blue color, an ELmax value of 447 nm and a CIE chromaticity (x,y) value of (0.19, 0.19). The external quantum efficiency of the device was 0.5%.

Example 3

A device was produced and evaluated in the same manner as in Example 2, except that 10 mg of Compound C, 5 mg of the present Compound (1-61) and 6 mg of Compound D were used in place of 20 mg of Compound C and 1 mg of the present Compound (1-61). As a result, blue luminescence having an ELmax of 447 nm and a CIE chromaticity (x,y) value of (0.19, 0.24) was obtained. The external quantum efficiency of this device was 1.3%.

Example 4

A cleaned ITO substrate was installed in a vacuum evaporation apparatus, and onto this substrate TPD (N,N'-diphenyl-N,N'-di(m-tolyl)benzidine) was evaporated into a 50 nm-thick film. Onto this film, Compound C and the present Compound (1-70) were evaporated simultaneously in a ratio of 17 to 1 (by mass), thereby forming a film having a thickness of 32 nm. Further thereon, a 36 nm-thick film of the azole Compound D was formed by vacuum evaporation, and subsequently thereto the same cathode as in Example 2 was formed by vacuum evaporation. The thus produced EL device provided blue luminescence having a CIE chromaticity value of (0.18, 0.36), and the external quantum efficiency thereof was 5.1%.

Compound C

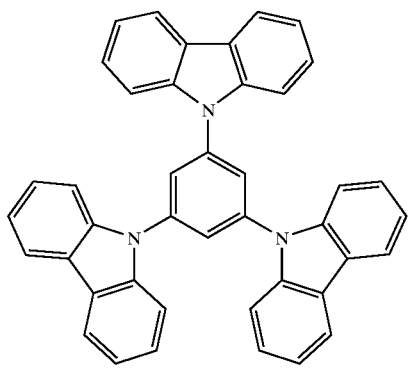

Compound D

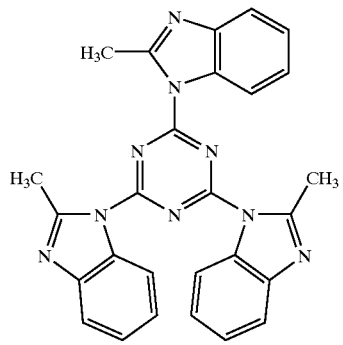

Similarly to the above, EL devices comprising other compounds according to the invention were produced and evaluated. As a result, it was confirmed that these devices were successful in producing blue luminescence although it had been difficult for hitherto known heavy metal complexes to enable the production of blue light-emitting devices. Further, it becomes possible to produce white light-emitting devices by applications of the present compounds. Furthermore, high-efficiency blue light-emitting devices which contain non-conjugate polymers (e.g., polyvinylcarbazole) and conjugate polymers (e.g., polyolefin compounds) and are formed using a coating technique can be produced by utilizing the present compounds.

The present blue light-emitting devices can be suitably used in various areas, such as those of indicators, displays, backlight, electrophotography, light sources for illumination, recording, exposure and reading uses, beacons, signboards and interiors. In addition, the present compounds are applicable to medical-care uses, brightening agents, photographic materials, UV absorbents, laser dyes, dyes for color filters, color conversion filters, and optical communications.

What is claimed is:

1. A light-emitting device comprising:
  a pair of electrodes; and
  organic compound layers comprising a light-emitting layer provided in between the electrodes,
  wherein at least one of the organic compound layers comprises a compound having a transition metal atom-phosphorus atom bond, and
  wherein the compound having a transition metal atom-phosphorus atom bond is represented by the following formula (2):

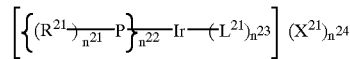 (2)

wherein $R^{21}$ represents a hydrogen atom or a substituent, $L^{21}$ represents a ligand, $X^{21}$ represents a counter ion, $n^{21}$ represents 2 or 3, $n^{22}$ represents an integer of 1 to 8, $n^{23}$ represents an integer of 0 to 8, $n^{24}$ represents an integer of 0 to 6, and, when $n^{21}$, $n^{22}$, $n^{23}$ or $n^{24}$ represents a plural number, $R^{21}$ groups, $(R^{21})_{n21}$—P ligands, $L^{21}$ ligands or $X^{21}$ ions are each the same or different.

2. The light-emitting device according to claim 1, wherein the luminescence spectrum of the device has a maximum emitted wavelength, λmax, in a range of 350 nm to 550 nm.

3. The light-emitting device according to claim 1, wherein the layer comprising the compound having a transition metal atom-phosphorus atom bond is a layer formed by a coating process.

4. The light-emitting device according to claim 1, wherein the compound having a transition metal atom-phosphorus atom bond is represented by the following formula (4):

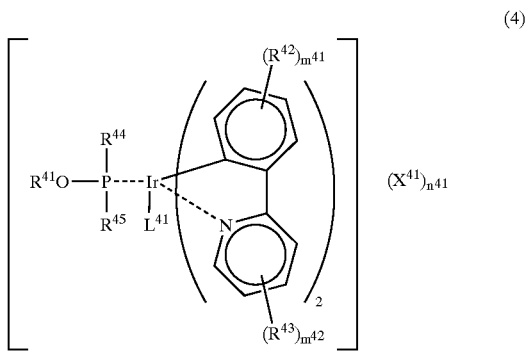

(4)

wherein $R^{41}$, $R^{42}$, $R^{43}$, $R^{44}$ and $R^{45}$ each independently represent a substituent, $L^{41}$ represents a ligand, $X^{41}$ represents a counter anion, $m^{41}$ and $m^{42}$ each independently represent an integer of 0 to 4, and $n^{41}$ represents 0 or 1.

5. The light-emitting device according to claim 4, wherein $L^{41}$ represents a halogen atom or a cyano group.

6. The light-emitting device according to claim 4, wherein the luminescence spectrum of the device has a maximum emitted wavelength, λmax, in a range of 350 nm to 550 nm.

7. The light-emitting device according to claim 4, wherein the layer comprising the compound represented by the formula (4) is a layer formed by a coating process.

8. The light-emitting device according to claim 1, wherein the compound having a transition metal atom-phosphorus atom bond is represented by the following formula (5):

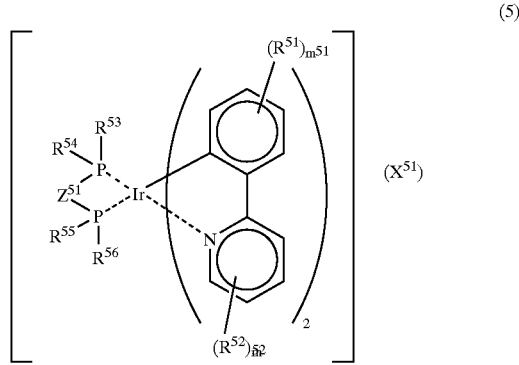

(5)

wherein $R^{51}$, $R^{52}$, $R^{53}$, $R^{54}$, $R^{55}$ and $R^{56}$ each independently represent a substituent, $Z^{51}$ represents a linkage group, $X^{51}$ represents a counter anion, and $m^{51}$ and $m^{52}$ each independently represent an integer of 0 to 4.

9. The light-emitting device according to claim 8, wherein $Z^{51}$ represents an alkylene group or an arylene group.

10. The light-emitting device according to claim 8, wherein the luminescence spectrum of the device has a maximum emitted wavelength, λmax, in a range of 350 nm to 550 nm.

11. The light-emitting device according to claim 8, wherein the layer comprising the compound represented by the formula (5) is a layer formed by a coating process.

12. The light-emitting device according to claim 8, wherein $Z^{51}$ represents an o-phenylene group.

13. The light-emitting device according to claim 1, wherein the compound having a transition metal atom-phosphorus atom bond is represented by the following formula (6):

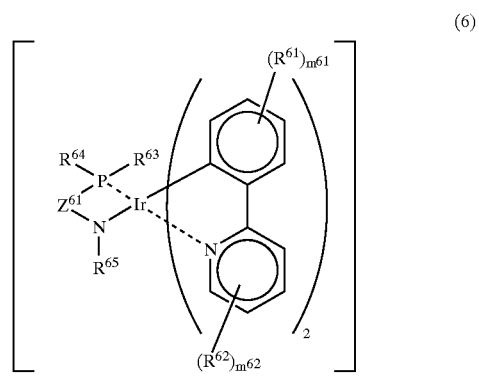

(6)

wherein $R^{61}$, $R^{62}$, $R^{63}$, $R^{64}$ and $R^{65}$ each independently represent a substituent, $Z^{61}$ represents a linkage group selected from an alkylene group, an alkenylene group, an arylene group, an oxygen linkage, a sulfur linkage and a linkage group having two or more of the above linkage groups therein, and $m^{61}$ and $m^{62}$ each independently represent an integer of 0 to 4.

14. The light-emitting device according to claim 13, wherein $Z^{61}$ represents an alkylene group or an arylene group.

15. The light-emitting device according to claim 13, wherein the luminescence spectrum of the device has a maximum emitted wavelength, λmax, in a range of 350 nm to 550 nm.

16. The light-emitting device according to claim 13, wherein the layer comprising the compound represented by the formula (6) is a layer formed by a coating process.

17. The light-emitting device according to claim 1, wherein the transition metal atom is an atom selected from the group consisting of ruthenium, rhodium, palladium, tungsten, rhenium, osmium, iridium and platinum.

18. The light-emitting device according to claim 1, wherein the phosphorus atom constitutes a part of phosphorus ligand.

19. The light-emitting device according to claim 18, wherein the phosphorus ligand is selected from the group consisting of an alkylphosphine and derivatives thereof, an arylphosphine and derivatives thereof, heteroarylphosphine and derivatives thereof, an alkoxyphosphine and derivatives thereof, an aryloxyphosphine and derivatives thereof, a heteroaryloxyaminophosphine and derivatives thereof, a phosphinine (phosphabenzene) and derivatives thereof, and aminophosphine and derivatives thereof.

20. The light-emitting device according to claim 1, wherein the x value on the CIE chromaticity diagram of the emitting device is 0.22 or less, and the y value on the CIE chromaticity diagram of the emitting device is 0.53 or less.

21. The light-emitting device, according to claim 1, wherein the luminescence spectrum of the device has a half band width of 1 nm to 100 nm.

22. The light-emitting device according to claim 1, wherein the valence number of iridium is trivalent.

23. The light-emitting device according to claim 1, wherein the content of the compound having a transition metal atom-phosphorus atom bond in the light-emitting layer is from 0.1% to 100% by weight based on the total composition of the light-emitting layer.

24. The light-emitting device according to claim 1, wherein the content of the compound having a transition metal atom-phosphorus atom bond in the light-emitting layer is from 1% to 50% by weight based on the total composition of the light-emitting layer.

25. The light-emitting device according to claim 1, wherein the content of the compound having a transition metal atom-phosphorus atom bond in the light-emitting layer is from 5% to 30% by weight based on the total composition of the light-emitting layer.

26. The light-emitting device according to claim 1, wherein at least one of $R^{21}$ represents a heteroaryl group.

27. The light-emitting device according to claim 1, wherein at least one of $R^{21}$ represents an alkoxy group.

28. The light-emitting device according to claim 1, wherein at least one of $R^{21}$ represents an aryloxy group.

29. The light-emitting device according to claim 1, wherein at least one of $R^{21}$ represents a heteroaryloxy group.

30. The light-emitting device according to claim 1, wherein at least one of $R^{21}$ represents a substituted amino group.

31. A compound represented by the following formula (4):

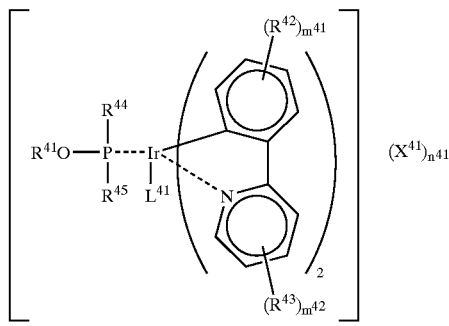

(4)

wherein $R^{41}$, $R^{42}$, $R^{43}$, $R^{44}$ and $R^{45}$ each independently represent a substituent, $L_{41}$ represents a ligand, $X^{41}$ represents a counter anion, $m^{41}$ and $m^{42}$ each independently represent an integer of 0 to 4, and $n^{41}$ represents 0 or 1.

32. A compound represented by the following formula (5):

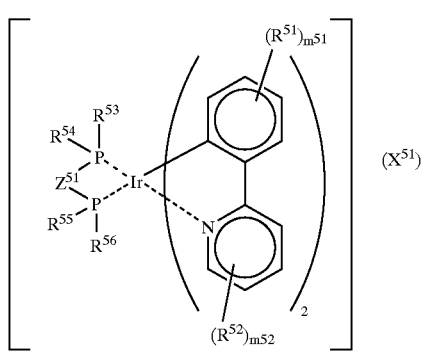

(5)

wherein $R^{51}$, $R^{52}$, $R^{53}$, $R^{54}$, $R^{55}$ and $R^{56}$ each independently represent a substituent, $Z^{51}$ represents a linkage group, $X^{51}$ represents a counter anion, and $m^{51}$ and $m^{52}$ each independently represent an integer of 0 to 4.

33. The light-emitting device according to claim 32, wherein $Z^{51}$ represents an o-phenylene group.

34. A compound represented by the following formula (6):

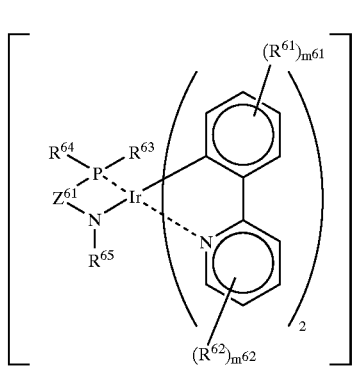

(6)

wherein $R^{61}$, $R^{62}$, $R^{63}$, $R^{64}$ and $R^{65}$ each independently represent a substituent, $Z^{61}$ represents a linkage group selected from an alkylene group, an alkenylene group, an arylene group, an oxygen linkage, a sulfur linkage and a linkage group having two or more of the above linkage groups therein, and $m^{61}$ and $m^{62}$ each independently represent an integer of 0 to 4.

35. A light emitting device comprising:
a pair of electrodes; and
organic compound layers comprising a light-emitting layer provided in between the electrodes,
wherein at least one of the organic compound layers comprises a compound having a transition metal-phosphorus atom bond, and
wherein the compound having a transition metal-phosphorus atom bond is represented by formula (1):

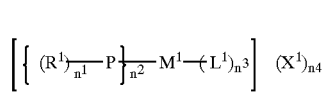

(1)

wherein $M^1$ represents transition metal ion, $R^1$ represents a hydrogen atom or a substituent, $L^1$ represents a halogeno ligand, a nitrogen-containing heterocycle ligand, a diketone ligand, a carboxylic acid ligand, a carbon monoxide ligand, an isonitrile ligand or a cyano ligand, $X^1$ represents a counter ion, $n^1$ represents 2 or 3, $n^2$ represents an integer of 1 to 8, $n^3$ represents an integer of 0 to 8, $n^4$ represents an integer of 0 to 6, when at least one of $n^1$, $n^2$, $n^3$ and $n^4$ is more than one, $R^1$ groups, $(R^1)_{n1}$—P ligand, $L^1$ ligands or $X^1$ ions are each the same or different.

36. The light-emitting device according to claim 35, wherein the transition metal ion is platinum or palladium.

37. The light-emitting device according to claim 35, wherein at least one of $R^1$ represents a heteroaryl group.

38. The light-emitting device according to claim 37, wherein the transition metal ion is platinum or palladium.

39. The light-emitting device according to claim 35, wherein at least one of $R^1$ represents a heteroaryloxy group.

40. The light-emitting device according to claim 39, wherein the transition metal ion is platinum or palladium.

41. The light-emitting device according to claim 35, wherein at least one of $R^1$ represents a substituted amino group.

42. The light-emitting device according to claim 41, wherein the transition metal ion is platinum or palladium.

43. The light-emitting device according to claim 35, wherein a plurality of $R^1$ combine with each other to form a cyclic structure.

44. The light-emitting device according to claim 43, wherein the transition metal ion is platinum or palladium.

45. The light-emitting device according to claim 35, wherein a plurality of $R^1$ combine with each other to form a phosphinine ring.

46. The light-emitting device according to claim 45, wherein the transition metal ion is platinum or palladium.

47. A light emitting device comprising:

a pair of electrodes; and organic compound layers comprising a light-emitting layer provided in between the electrodes, wherein at least one of the organic compound layers comprises a compound having a transition metal-phosphorus atom bond, and wherein the compound having a transition metal-phosphorus atom bond is represented by formula (1):

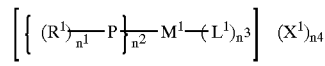

(1)

wherein $M^1$ represents ruthenium, rhodium, tungsten, rhenium or osmium, $R^1$ represents a hydrogen atom or a substituent, with the proviso that at least one of $R^1$ represents a heteroaryl group, $L^1$ represents a ligand, $X^1$ represents a counter ion, $n^1$ represents 2 or 3, $n^2$ represents an integer of 1 to 8, $n^3$ represents an integer of 0 to 8, $n^4$ represents an integer of 0 to 6, when at least one of $n^1$, $n^2$, $n^3$ and $n^4$ is more than one, $R^1$ groups, $(R^1)_{n1}$—P ligand, $L^1$ ligands or $X^1$ ions are each the same or different.

48. A light emitting device comprising:

a pair of electrodes; and organic compound layers comprising a light-emitting layer provided in between the electrodes, wherein at least one of the organic compound layers comprises a compound having a transition metal-phosphorus atom bond, and wherein the compound having a transition metal-phosphorus atom bond is represented by formula (1):

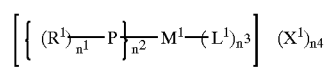

(1)

wherein $M^1$ represents ruthenium, rhodium, tungsten, rhenium or osmium, $R^1$ represents a hydrogen atom or a substituent, with the proviso that at least one of $R^1$ represents a heteroaryloxy group, $L^1$ represents a ligand, $X^1$ represents a counter ion, $n^1$ represents 2 or 3, $n^2$ represents an integer of 1 to 8, $n^3$ represents an integer of 0 to 8, $n^4$ represents an integer of 0 to 6, when at least one of $n^1$, $n^2$, $n^3$ and $n^4$ is more than one, $R^1$ groups, $(R^1)_{n1}$—P ligand, $L^1$ ligands or $X^1$ ions are each the same or different.

49. A light emitting device comprising:

a pair of electrodes; and organic compound layers comprising a light-emitting layer provided in between the electrodes, wherein at least one of the organic compound layers comprises a compound having a transition metal-phosphorus atom bond, and wherein the compound having a transition metal-phosphorus atom bond is represented by formula (1):

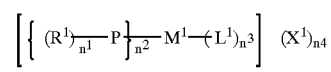

(1)

wherein $M^1$ represents ruthenium, rhodium, tungsten, rhenium or osmium, $R^1$ represents a hydrogen atom or a substituent, with the proviso that at least one of $R^1$ represents a substituted amino group, $L^1$ represents a ligand, $X^1$ represents a counter ion, $n^1$ represents 2 or 3, $n^2$ represents an integer of 1 to 8, $n^3$ represents an integer of 0 to 8, $n^4$ represents an integer of 0 to 6, when at least one of $n^1$, $n^2$, $n^3$ and $n^4$ is more than one, $R^1$ groups, $(R^1)_{n1}$—P ligand, $L^1$ ligands or $X^1$ ions are each the same or different.

50. A light emitting device comprising:

a pair of electrodes; and organic compound layers comprising a light-emitting layer provided in between the electrodes, wherein at least one of the organic compound layers comprises a compound having a transition metal-phosphorus atom bond, and wherein the compound having a transition metal-phosphorus atom bond is represented by formula (1):

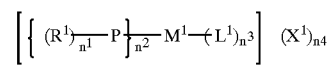

(1)

wherein $M^1$ represents ruthenium, rhodium, tungsten, rhenium or osmium, $R^1$ represents a hydrogen atom or a substituent, with the proviso that a plurality of $R^1$ combine with each other to form a phosphinine ring, $L^1$ represents a ligand, $X^1$ represents a counter ion, $n^1$ represents 2 or 3, $n^2$ represents an integer of 1 to 8, $n^3$ represents an integer of 0 to 8, $n^4$ represents an integer of 0 to 6, when at least one of $n^1$, $n^2$, $n^3$ and $n^4$ is more than one, $R^1$ groups, $(R^1)_{n1}$—P ligand, $L^1$ ligands or $X^1$ ions are each the same or different.

* * * * *